United States Patent
Burns et al.

(10) Patent No.: US 8,366,625 B2
(45) Date of Patent: Feb. 5, 2013

(54) ULTRASOUND MOLECULAR SENSORS AND USES THEREOF

(75) Inventors: David Burns, Montreal (CA); David Troiani, Pierrefonds (CA); Jonathan Dion, Montreal (CA)

(73) Assignee: McGill University, Montréal, QC (CA)

( * ) Notice: Subject to any disclaimer, the term of this patent is extended or adjusted under 35 U.S.C. 154(b) by 824 days.

(21) Appl. No.: 12/224,928

(22) PCT Filed: Mar. 5, 2007

(86) PCT No.: PCT/IB2007/000506
§ 371 (c)(1),
(2), (4) Date: Dec. 12, 2008

(87) PCT Pub. No.: WO2007/105047
PCT Pub. Date: Sep. 20, 2007

(65) Prior Publication Data
US 2009/0299190 A1    Dec. 3, 2009

Related U.S. Application Data

(60) Provisional application No. 60/780,823, filed on Mar. 10, 2006.

(51) Int. Cl.
*A61B 8/14* (2006.01)
(52) U.S. Cl. .................... 600/458; 600/437; 424/9.5
(58) Field of Classification Search .................... 600/437, 600/458; 424/1.29, 1.49, 9.1, 9.322, 9.34, 424/9.341, 9.35, 9.351, 9.5, 9.51, 9.52
See application file for complete search history.

(56) References Cited

U.S. PATENT DOCUMENTS

| | | | |
|---|---|---|---|
| 5,411,730 A * | 5/1995 | Kirpotin et al. | 424/9.322 |
| 6,245,318 B1 | 6/2001 | Klibanov et al. | |
| 6,423,296 B1 * | 7/2002 | Gunther et al. | 424/9.322 |
| 7,769,423 B2 * | 8/2010 | Viglianti et al. | 600/407 |
| 2001/0012522 A1* | 8/2001 | Ottoboni et al. | 424/501 |
| 2005/0074499 A1* | 4/2005 | Tagawa et al. | 424/489 |
| 2008/0019904 A1* | 1/2008 | Boehmer et al. | 424/1.29 |

FOREIGN PATENT DOCUMENTS

| | | |
|---|---|---|
| WO | 98/53857 | 12/1998 |
| WO | 03/082117 | 10/2003 |
| WO | 2006/003581 | 1/2006 |

OTHER PUBLICATIONS

English language version of the Japanese Office Action dated May 17, 2012 for Japanese Patent Application No. 2008-557844.

* cited by examiner

*Primary Examiner* — Brian Casler
*Assistant Examiner* — Amanda Lauritzen
(74) *Attorney, Agent, or Firm* — Bereskin & Parr LLP/S.E.N.C.R.L., s.r.l.; Stephen Beney

(57) ABSTRACT

The present invention relates to the use of polymers as contrast agents for ultrasounds. The idea is to have a molecular imprint in the polymer that is specific for a given molecule or analyte. When that molecule binds to the polymer it induces a conformational change that results in an increase in the ultrasound signal, referred to as a target-bound state. The method can also be used for example for quantitative measurements of analytes.

13 Claims, 28 Drawing Sheets

Poly
(N-isopropylacrylamide)
(NIPA)

A.
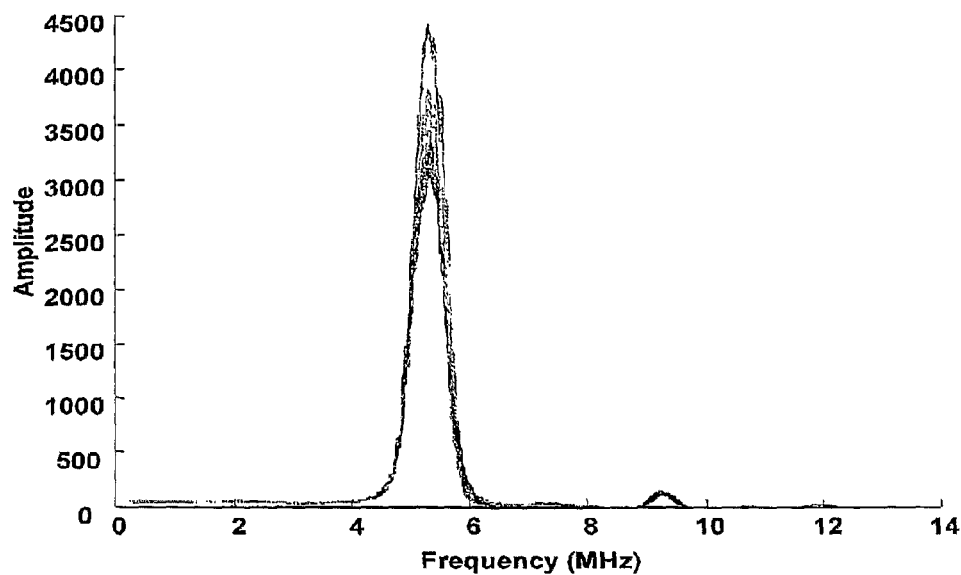
B.
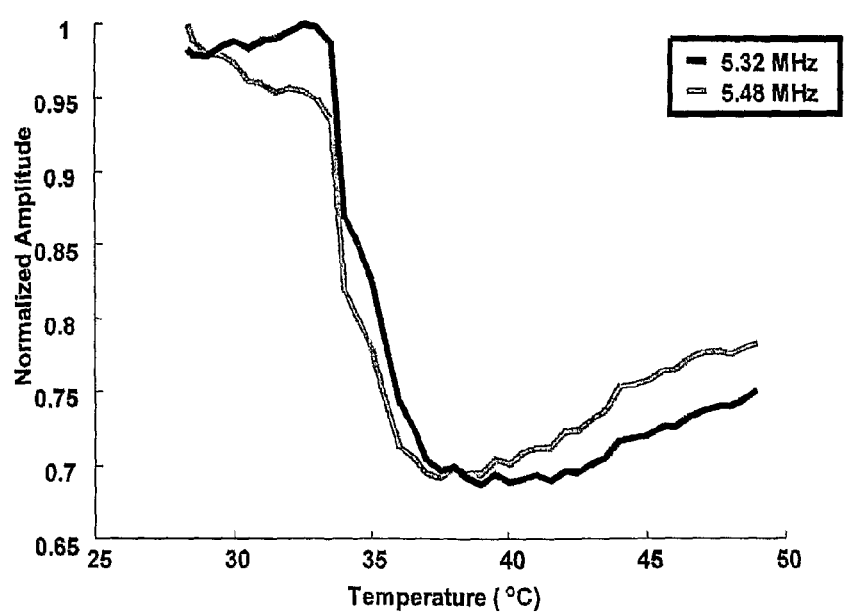
FIGURE 5

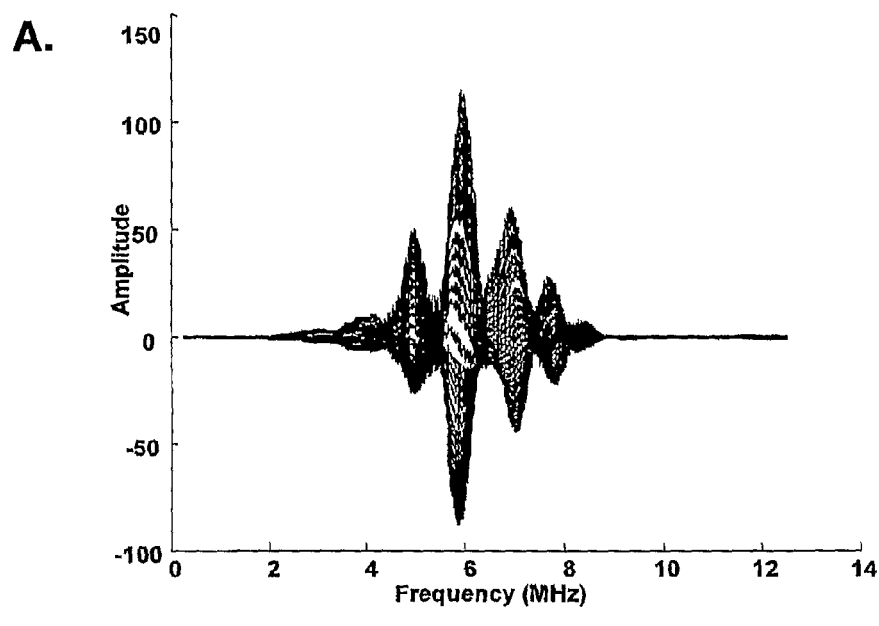
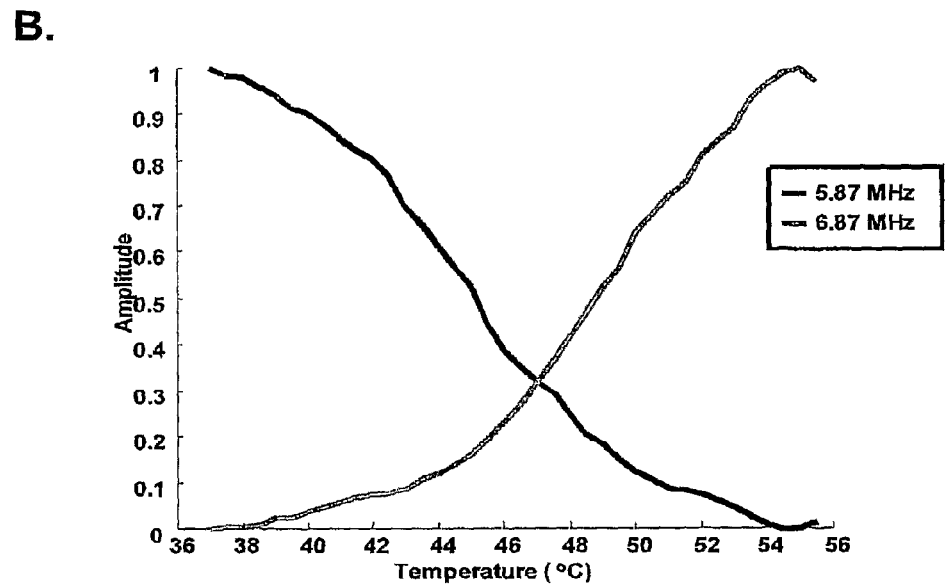
FIGURE 7

Theophylline     Caffeine

Carboxymethyl Cellulose (CMC) affixed with TNF-α antibodies

- Selective molecular "pockets" designed by biological systems!

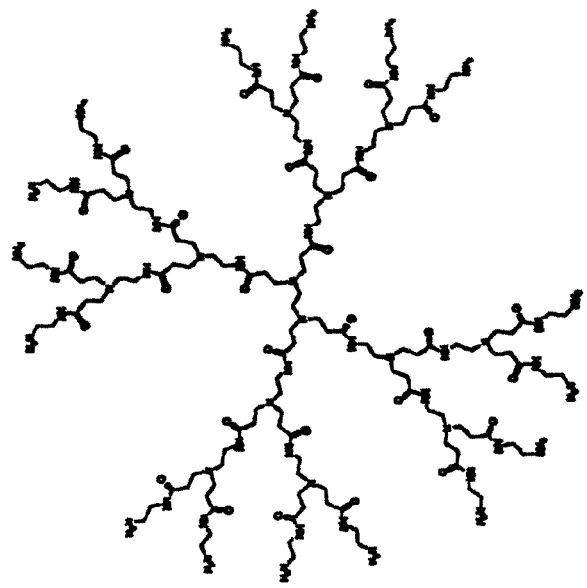
- Increasing monodispersity should improve sensitivity
  → Dendrimers have well-controlled polymeric structure
- Poly-amidoamine dendrimers are biocompatible[5]
  → Same antibody linking procedures
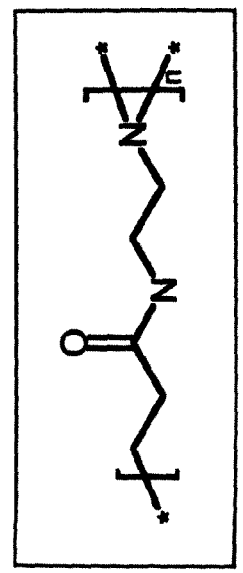
FIGURE 30

ULTRASOUND MOLECULAR SENSORS AND USES THEREOF

RELATED APPLICATIONS

This application is a Patent Cooperation Treaty Application which claims the benefit of 35 U.S.C. 119 and/or §120 based on the priority of co-pending U.S. Provisional Patent Application No. 60/780,823 filed Mar. 10, 2006, which is herein incorporated by reference in its entirety.

FIELD OF THE INVENTION

The invention relates to ultrasound based detection and quantification methods as well as compounds useful in the ultrasonic detection of analytes.

BACKGROUND OF THE INVENTION

Ultrasound has been established in the field of medicine for many years, mainly used as an imaging method to help monitor the status of a woman's fetus. The term ultrasound can be defined as sound with a frequency higher than that perceivable by the human ear (a range of roughly 20 Hz to 20 kHz). Medical ultrasound imaging and associated research typically takes place in the 1 MHz to 10 MHz range.

The first application of this technique in the field of medicine can be attributed to Dr. Karl Theodore Dussik. In 1952, Austria, he pioneered the field of medical ultrasonics, recounting his work done on transmission ultrasound through the brain, Professor Ian Donald further explored other applications of this technique in the late 50's and 60's. After extensive testing on abdominal masses, he conducted the very first trial of medical ultrasound on a pregnant woman in 1958.

Ultrasound techniques for medical applications have become popular due to the ease of use and non-invasive features. Ensuing years brought many improvements to the ultrasound probes, enabling higher resolution images.

When ultrasound strikes a surface object, some of it is reflected, scattered, or transmitted through the object, much like light passing through a lens. This sound is also attenuated when hitting the surface, with higher frequencies affected more than lower frequencies. Low frequency sounds can therefore traverse more layers of matter before being attenuated completely.

In medical ultrasonics, ultrasound is created by a transducer, a tiny piezoelectric device mounted inside a probe. When a current is run through this device, it vibrates at a specific frequency, generating ultrasound waves that emanate in the direction of the probe. The probe also doubles as an ultrasonic detector. When ultrasound hits the piezoelectric device, it vibrates and generates a current.

To ensure that high frequency ultrasonic waves propagate through tissue while minimizing attenuation due to striking a surface, clinical ultrasound probes need to be water-coupled to the tissue body being analyzed. This is achieved using an ultrasound gel, a substance rubbed onto the skin of a patient to provide full contact with the ultrasound probe.

An image can be generated from ultrasound by analyzing the reflections once it has propagated through layers of tissue. The time it takes for the reflections to return to the probe indicates the distance which the ultrasound pulse has traveled. Multiple layers of tissue can be perceived by scanning one spot of the body and listening to the multiple reflections returning to the probe. A complete image can also be generated by scanning a section of the body and aligning all the data from the ultrasonic reflections.

The integration of ultrasonic imaging in the field of medicine allowed a step by step approach to prenatal care in the womb. However, this type of imaging does have some drawbacks.

The first is the tradeoff between depth and resolution. As previously stated, lower frequency sounds (longer wavelength) travel deeper into objects, while higher frequencies (shorter wavelength) reveal very fine details, increasing imaging resolution.

To obtain the best possible resolution, it is preferable to uses a high frequency ultrasound. However, such high frequency ultrasound is attenuated very quickly and therefore does not penetrate very far into the human body. In order to traverse several levels of tissue and organs while still providing reasonable imaging capabilities, the frequency must be lowered, thereby sacrificing resolution.

The second major limitation relates to the lack of molecular modulation provided by medical ultrasound. Ultrasonic tissue imaging is very effective at illustrating the state of internal body parts as well as fetuses, however no modulation is gained by present methods of ultrasound with respect to the concentration of any specific molecules in the circulation or in tissues or organs. Other more invasive and often less desirable means are used when this modulation is required.

Therefore, there is a need for improved methods of detection using ultrasound devices.

SUMMARY OF THE INVENTION

In a broad aspect of the invention there is provided a method for detecting, identifying and quantifying analytes using ultrasound spectral characteristics. The method advantageously provides molecular modulation using ultrasonic probing of samples.

In one embodiment of the invention there is provided a method for ultrasound contrast enhancement, comprising:
  providing an ultrasound molecular sensor comprising one or more target binding sites for binding one or more target molecules, the ultrasound molecular sensor having target-bound and target-unbound states wherein binding of the one or more target molecules to the ultrasound molecular sensor causes a modulation in an ultrasound signal;
  contacting the ultrasound molecular sensor with the one or more target molecules to produce ultrasound molecular sensor in the target-bound state; and
  obtaining an ultrasound signal of the target-bound ultrasound molecular sensor at one or more ultrasound frequencies wherein the signal comprises a modulation indicative of the presence of at least one target molecule.

In another embodiment there is provided a method for detecting an analyte, comprising:
  contacting the analyte with an ultrasound molecular sensor comprising one or more analyte binding sites for binding one or more analytes, the ultrasound molecular sensor having analyte-bound and analyte-unbound states wherein binding of the one or more analyte to the ultrasound molecular sensor causess a modulation in ultrasound signal; and
  obtaining an ultrasound signal of the analyte-bound state at one or more frequencies wherein the signal comprises modulation indicative of the presence of the analyte.

In yet another embodiment there is provided a compound comprising a ultrasound molecular sensor and analyte binding sites coupled to the ultrasound molecular sensor; the compound having target-bound and target-unbound states, wherein the target-unbound state is substantially transparent to ultrasound and the target-bound state is ultrasound sensitive, and wherein the analyte binding sites are in sufficient number for producing a detectable ultrasound signal at characteristic frequencies when molecules of analytes are bound to the analyte binding sites, thereby causing the compound to be in a target-bound state.

BRIEF DESCRIPTION OF THE DRAWINGS

Further features and advantages of the present invention will become apparent from the following detailed description, taken in combination with the appended drawings, in which:

FIGS. 5A and B FTs of reflectance measurements at various temperatures for NIPA;
FIGS. 7A and B FTs of transmission measurements at various temperatures for HPC;
FIG. 30 is a schematic diagram of a dendrimer polymer.

DETAILED DESCRIPTION OF THE INVENTION

Figure 1:
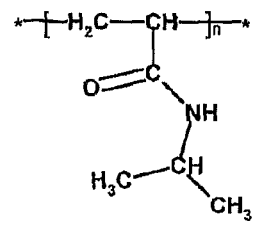
FIG. 1 is an N-isopropylacrilamide (NIPA) hydrogel.

In the present description by ultrasound molecular sensor it is meant any molecule that can produce and ultrasound signal upon being appropriately excited. As used herein, ultrasound molecular sensor comprises but is not limited to large organic molecules such as polymers including but not limited to hydrogel polymers such as polyacrylamide, cellulose, alginates and the like, non-hydrogel polymers and dendrimers.

By target molecule it is meant molecules capable of binding to an ultrasound molecular sensor to cause ultrasound modulations. Such target molecules may include but are not limited to biological molecules such as proteins, hormones and the like.

By analyte it is meant any molecule that is determined analytically by the method of the invention. It will be appreciated that in some instances target molecules may be analytes when it is desired for example to measure their concentration.

There is provided a method for ultrasound contrast enhancement using an ultrasound molecular sensor for proving contrast enhancement in ultrasound imaging and quantification of analytes.

There is provided a method for detecting and quantifying analytes using ultrasound frequencies measurements. In one aspect of the invention it was advantageously discovered that when an analyte is contacted with a ultrasound molecular sensor having binding sites for the analyte there results a ultrasound molecular sensor-analyte composition that exhibits a characteristic ultrasound spectrum when excited with ultrasounds. By characteristic ultrasound spectrum it is meant that the composition exhibits unique ultrasound spectral profile. Furthermore, the invention provides for the quantification of analytes using spectral bands.

The ultrasound molecular sensors that are suitable for the detection and quantification of analytes are ultrasound molecular sensors that exhibit an ultrasound spectrum upon pressure excitation by an ultrasound wave and that possess binding sites for an analyte. The nature of the binding sites will vary depending on the analyte to be detected and the molecular composition of the ultrasound molecular sensor. The ultrasound molecular sensor can be treated or derivatized to incorporate analyte binding sites. The binding sites can be selected from a number of possible types such as antibodies or part thereof, proteins or part thereof, nucleic acids, carbohydrates, functional groups having specific physico-chemical properties and the like. For example, a receptor protein can be coupled to the ultrasound molecular sensor thereby allowing biding of the corresponding ligand.

In another approach the biding site may be created by molecular imprinting or constrained self-assembly by incubating the ultrasound molecular sensor with the ligand to produce biding sites.

The ultrasound molecular sensor may be any suitable ultrasound molecular sensor provided that it can produce an ultrasound spectrum upon excitation by an ultrasound pulse and that binding of the analyte to the ultrasound molecular sensor produces a spectrum characteristic of the presence of the analyte.

In a preferred embodiment, an ultrasound molecular sensor is a hydrogel polymer such as but not limited to polyacrylamide and cellulose polymers having multiple binding sites for the analyte. Polymers may also include dendrimers.

Detection of the ultrasound signal from the ultrasound molecular sensor or ultrasound molecular sensor-analyte complex requires excitation to induce vibrations in the ultrasound molecular sensor capable of producing ultrasound waves. In a preferred embodiment the excitation is provided by ultrasounds, preferably a pulsed ultrasound. Ultrasounds can be detected in the transmission or the reflection configuration. Choice of the configuration can be made based on the nature of the sample to be analyzed. Liquid solutions are amenable to transmission detection but detection within an individual for example may require the use of reflection configuration.

In one embodiment transmission measurements are performed using a pulsed ultrasound generated at a transducer to excite the ultrasound molecular sensor-analyte complex into high frequency vibrations which in turns generate ultrasounds that are detected using a second transducer. The transducers preferably operate at between 1 and 10 MHZ. But it will be appreciated that the actual frequency of excitation depends on the type of ultrasound molecular sensor and the depth at which the ultrasound molecular sensor-analyte complex is located relative to the transducer.

Typically, as used for example in ultrasound imaging, the transducer sends out a fundamental beam and receives essentially the same frequency range back as an echo (or as a transmission signal in case of transmission geometry). However, the sound wave becomes distorted as the tissue or the molecular complex expands and compresses in response to the wave. When a certain energy level is reached, this distortion results in the generation of additional frequencies, called harmonics, that are two, three or more times the emitted frequency. The harmonic frequencies return to the transducer together with the fundamental frequency. In the present invention it has been discovered that enharmonic frequencies (frequencies other than the harmonic frequencies) are useful in the detection and quantification of analytes.

As mentioned above, it was advantageously discovered that the intensity of some of the frequency bands in the ultrasound spectrum is proportional to the concentration of the analyte. Thus the method also provides for the quantification of the analyte using one or more frequency bands that are shown to correlate with the concentration of the analyte. The quantification of an analyte in a solution of unknown concentration can be done by establishing a standard curve, by using an internal standard or by establishing a linear combination of several frequencies to obtain an equation that computes the concentration of an analyte.

Thus the process of detecting or quantifying an analyte using the method of the present invention may comprise contacting the analyte with an appropriate ultrasound molecular sensor having analyte binding sites and obtaining an ultrasound signal at one or more frequencies to detect or quantify the analyte. For detecting the presence of an analyte the ultrasound signal is inspected for its modulation content. By modulation it is meant the presence or absence of signal at certain frequencies, the intensity of the frequencies, frequency shifts and the like. It will be appreciated that when an analyte is analyzed for the first time it may be necessary to acquire an ultrasound signal comprising multiple frequencies to enable comparison with the spectrum of the agent without analyte and therefore identify by comparing the spectra, the frequencies that are characteristic of the presence of the analyte. While a single frequency may provide enough modulation to identify an analyte, in some cases the relative intensity of two or more frequencies is necessary to distinguish between analytes. The use of multiple frequencies may also increase the reliability of the detection. For quantification of a known analyte it may be possible to use a single frequency the amplitude of which has been shown to correlate with the concentration of the analyte. However establishing a correlation using a linear combination may provide more accurate results.

In another embodiment, changes in the ultrasound signal (acoustic properties) of a ultrasound molecular sensor, with or without the presence of an analyte, may be caused for example by changes in the conformational folding of the ultrasound molecular sensor and/or its rigidity. Thus molecular changes in the ultrasound molecular sensor may result in changes in acoustic properties. For example, it may be possible to detect the presence of reactive molecules, for example free radicals, such as nitric oxide because of their degrading effect on the molecular structure of the ployner. It will be appreciated that ultrasound molecular sensors may be designed to be sensitive to such molecules.

Various ultrasound molecular sensors may be used for the detection of an analyte each ultrasound molecular sensor exhibiting a characteristic spectrum. Similarly a ultrasound molecular sensor may be capable of binding different analytes to generate characteristic spectra. When spectra of different analyte obtained with the same ultrasound molecular sensor are compared, similarity can indicate similarities in the analyte structure. Thus the method of the invention may also be used to identify or help in the identification of unknown analytes.

The ultrasound molecular sensor of the invention can be used in a variety of ways. By way of examples they can be used for detection and quantification of analyte in mixtures. This particular application is useful in chemistry, environmental analyses and the like. By selecting a biocompatible ultrasound molecular sensor, it can be used to detect and quantify analyte within a subject such as a human. Furthermore it can also serve as a contrast agent by biding analytes (or more generally molecules) that are found in specific anatomical structures.

Thus the ultrasound molecular sensor can be used in vivo for the detection of an analyte. When use in an animal or human body the ultrasound molecular sensor ultrasound agent of the invention can be injected by methods that are well known in the art such as aerosol inhalation, injection and ingestion. Preferably, the ultrasound molecular sensors of the present invention are administered to a subject by subcutaneous (s.c.), intraperitoneal (i.p.), intra-arterial (i.a.), or intravenous (i.v.) injection. The ultrasound molecular sensor is also preferably administered using a pharmaceutically acceptable carrier which can be sterilized by techniques known to those skilled in the art. Pharmaceutically acceptable carrier are known to those skilled in the art and may include saline solutions, liposomal preparation and the like. Samples may also be obtained from individuals and analytes measured directly in the sample.

The ultrasound molecular sensor-analyte complex will exhibit variable diameters depending on the actual composition and concentration as well as the physico chemical conditions. It will be appreciated that the size of the ultrasound molecular sensor and the ultrasound molecular sensor-analyte complex as well as its molecular composition can influence the pharmacodynamic properties of the compound. By pharmacodynamic properties it is meant the biodistribution of the compound as well as properties such as kinetics of clearance from blood or excretion from the kidney, stability and the like. One of skills in the art can optimize the composition so as to fully exploit the advantages of the invention.

Some examples of the possible in vivo use of the invention are detection/quantification of drugs, detection/quantification of physiological molecules (hormones, protein, vitamins and the like), temperature detection within organs (using phase transition properties of the ultrasound molecular sensor).

In another aspect of the invention there is also provided an apparatus for obtaining ultrasound measurements from various samples. The apparatus comprises ultrasounds emitting and detecting transducers that can be controlled to emit and detect at a predetermined frequency or range of frequencies. The apparatus further comprises analyzer/processor to identify/record the ultrasound signal as a function of frequency. The analyzer/processor may also comprise means to identify or distinguish between harmonic and enharmonic frequencies. In a preferred embodiment the apparatus also comprises a processor for calculating the concentration of analyte based on the ultrasound signal. The apparatus may function in the transmission or reflection mode depending on the sample being analyzed. Transmission configuration may be used for samples such as aqueous solutions while reflection is more suitable for obtaining measurements from an animal such as a human.

The present invention will be more readily understood by referring to the following examples which are given to illustrate the invention rather than to limit its scope.

EXAMPLES

Example 1

Certain polymer gels respond to external stimuli, in the form of changes in the surrounding environment. Temperature, pH, solvent concentrations, type of solvent, electric fields, and light are a few parameters that can cause these polymer gels to change their characteristics when adjusted. N-isopropylacrilamide (NIPA) is one such polymer gel (FIG. 1), also known as a hydrogel, and it has been extensively studied due to its unusual properties.

This particular hydrogel can undergo an impressive large reversible change in volume and properties when temperature is increased beyond a critical point. This critical temperature, Tc, was investigated by Shibayama and Tanaka and found to be 34° C. Below Tc, the hydrogel is a clear, transparent solution, with a viscosity similar to that of water. At the molecular level, its configuration takes the form of a swollen network of interconnected polymer chains, with solvent molecules flowing freely between them.

Figure 2:
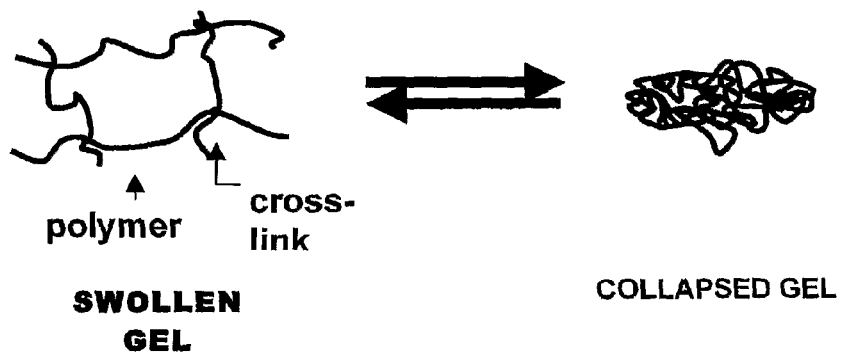
FIG. 2 is an illustration of phase transition hydrogel states.

Once the hydrogel is heated above Tc, the swollen network collapses to form small domains of concentrated polymer chains (FIG. 2) of a broad size distribution. As a result, the hydrogel solution becomes populated with an non-homogeneous mixture of lightly and heavily cross-linked regions, as some areas collapse more than others. The process of undergoing this collapse is known as a phase transition, or more technically, spinodal decomposition, the onset of which is the change from transparent to turbid.

The spatial inhomogeneity present in the collapsed phase not only causes the solution to become turbid, scattering visible light, but also changes many properties of the hydrogel, including ultrasonic characteristics, as discussed a later section. It is also interesting to note that if the temperature is increased at an extremely slow rate (0.1° C. per day), the sample becomes unquenched. Consequently, the small domains present in the solution will have enough time to diffuse, and the polymer network equilibrates, demonstrating very similar properties seen with a temperature below Tc. This is evident when considering slow movements of the small domains caused by small concentration gradients. Once the gradients have diffused completely, the gel is homogeneous and transparent, similar to its state at room temperature.

The hydrogen bonds that keep the gel swollen at room temperature become overpowered by thermal energy. Interactions between the polymer chains are therefore more prominent, causing the gel to collapse on itself. The volume inside the domain is initially constant (isochore) since solvent molecules are trapped inside during the collapse.

These properties of NIPA have generated many applications such as shape memory gels, where a modulated polymer synthesis technique was invoked to develop gels that change from a rod-like shape to various complex forms. Other interesting functions for NIPA include a thermally responsive attenuator for ultrasound waves, an optical switch, and photoresistive artificial muscles.

It is also worth noting that hydropropyl cellulose (HPC) seems to exhibit properties similar to NIPA, although the phase transition is not visually as pronounced.

Example 2

Figure 3:
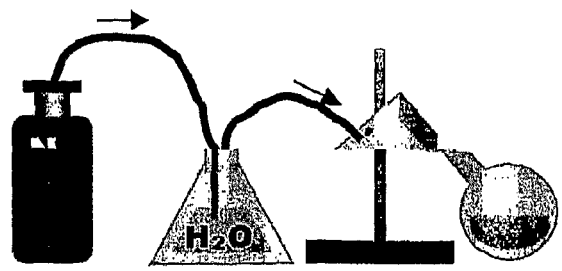
FIG. 3 is a hydrogel nitrogen purging setup.

The procedure for synthesizing the NIPA hydrogel was adapted from Hu's work. N-isopropylacrylamide (NIPA, 2 g) and N,N'-methylene-bis-acrylamide (MBA, 0.033 g) were added to a flask containing roughly 50 mL of water, and the resulting solution stirred until complete dissolution. Since any trace of oxygen can ruin the polymerization step, oxygen removal was accomplished by blowing nitrogen over the solution as it was turned by a customized rotary evaporator (FIG. 3). In order to prevent the solution from evaporating under the constant stream of nitrogen, it was first bubbled through a flask of water. This method was found to be more efficient than simply bubbling nitrogen through the solution, taking a mere 3 hours instead of purging overnight.

Once purging was complete, tetramethylethylenediamine (TMED, 60 µL) was added to the solution as the polymerization accelerator. Ammonium persulfate ($(NH_4)_2S_2O_8$, 0.015 g) was then introduced to initiate the radical polymerization, and the mixture was gently stirred. After about 20 minutes of settling, the solution turned slightly cloudy white denoting the presence of the NIPA hydrogel. Heating the solution to 45° C. induced a phase transition, and the solution turned cloudy white.

If too much water was added at the beginning, the polymerized solution might still be colorless transparent even though the polymerization was successful. Applying heat to induce a phase transition as noted above will confirm the presence of the hydrogel, as the solution should still turn opaque white, although to a lesser degree.

Example 3

The procedure for synthesizing the HPC hydrogel is as follows: Hydropropyl cellulose (0.1 g) was added to a flask containing 100 mL of water. This solution's pH was adjusted to 12 through the addition of potassium hydroxide (KOH), and the mixture was stirred in darkness for 4 days.

After this time elapsed, dodecyltrimethyl-ammonium bromide (DTAB, 0.35 g) was added to the solution and stirred for an additional hour. Divinylsulfone (DVS, 0.04 g) was added to the flask and the contents were heated to 55° C. for 30 seconds to initiate the polymerization. The solution was then quickly acidified with concentrated hydrochloric acid (HCl) to stop the polymerization.

Example 4

One aim of this experiment was to acquire ultrasound scans at temperatures above and below $T_c$ for the NIPA hydrogel to characterize its ultrasonic properties.

The entire ultrasound system used in this experiment consisted of a 5 MHz clinical ultrasound transducer, a sample cell, a signal pulse generator/amplifier (Panametrics Inc.), an SDS 200 oscilloscope (SoftDSP Co.), a thermocouple temperature sensor connected to a multimeter, and a computer.

Figure 4:
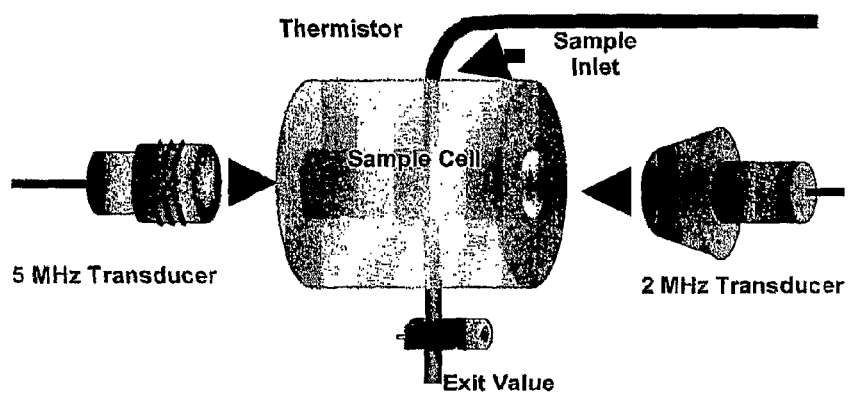
FIG. 4 is a flow sample cell experiment setup.

The sample cell consisted of a flow cell modified in order to have full contact between the hydrogel samples and the clinical probe, for proper water-coupling to occur (FIG. 4).

As illustrated in the above figure, this modified cell did not have heating capabilities. Consequently, the solutions were heated in a water bath to 65° C., transferred to the sample cell with a loss of roughly 10-15° C., and data was recorded every 30 seconds as they cooled to 28° C.

The same ultrasound transducer was used to pulse the hydrogel samples and record the data, thereby measuring reflectance signals. This ultrasound data was acquired by the oscilloscope at a sampling rate of 12.5 MHz, no signal damping, and 128 averages per scan using SoftDSP's Softscope acquisition program. MatLab was used to import the data and perform data processing, such as constructing Fourier transforms and boxcar smoothing the data. The results of the reflectance measurements, summarized in FIGS. 5A and B show the expected sharp signal attenuation at 34° C. for the NIPA hydrogel, which is consistent with Hu's work.

The second study aimed to further explore the ultrasonic characteristics of both NIPA and HPC hydrogels. This was achieved by rearrangement one experimental parameter, in this case, pulsing the samples with a 2 MHz clinical ultrasound probe and receiving the signal with the previously used 5 MHz probe, which measures transmission data. Acquisition parameters were left unchanged from the first study.

Figure 6:
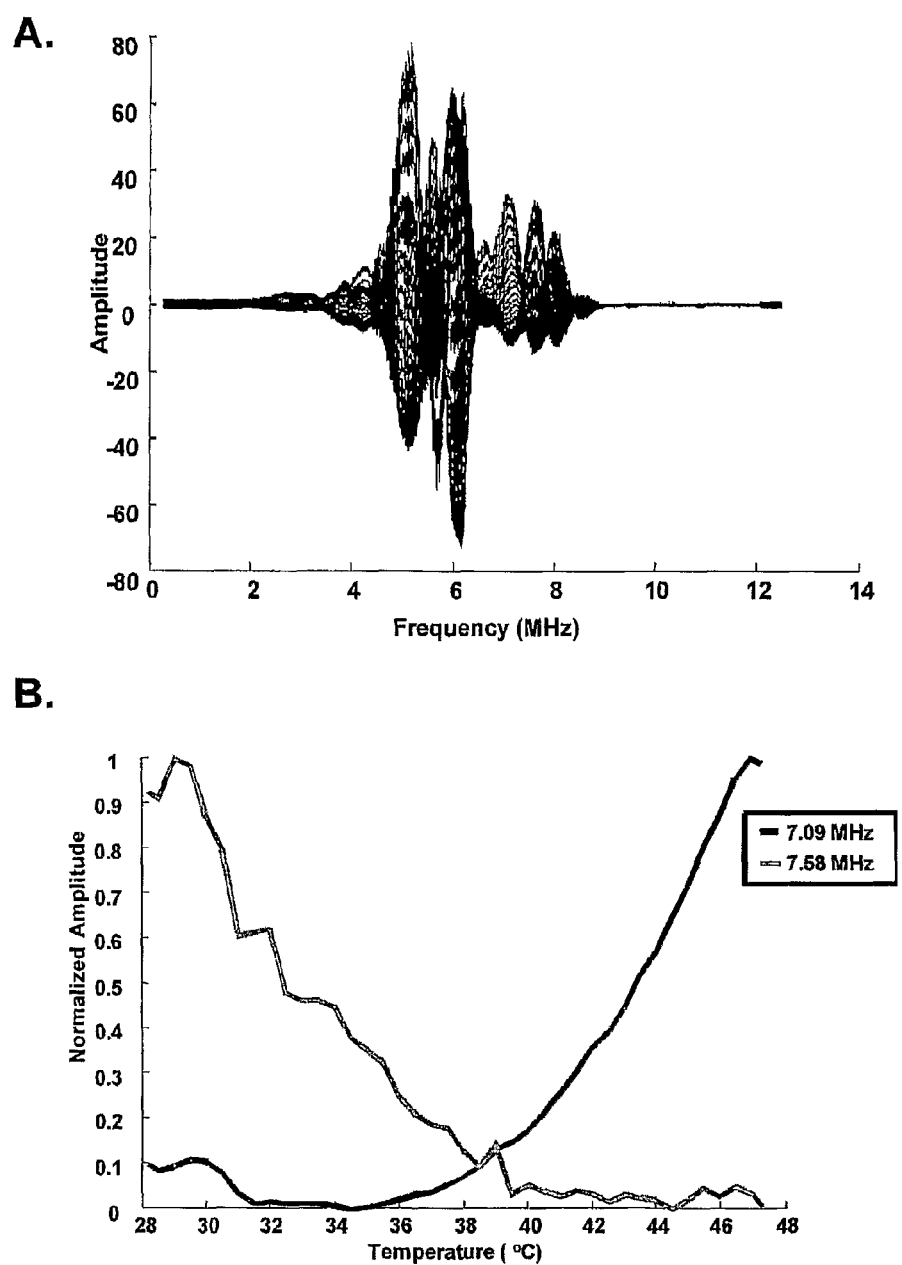
FIGS. 6A and B FTs of transmission measurements at various temperatures for NIPA.

The results of the scans provided much more modulation than the reflectance measurements, as shown in FIGS. 6A and B and 7A and B. This data was smoothed as previously done, and mean centered so that only changes in frequency amplitudes were made visible.

Both hydrogels showed multiple ultrasound frequency interactions as a result of undergoing a phase transition. Frequency shifts were clearly visible, demonstrated by frequency attenuation in certain places, and frequency amplification in others. Another interesting result is that while harmonic interactions were noted (harmonic denoting multiples of the pulsing frequency), enharmonic interactions were also displayed. This is emphasized to a greater extent when looking at the amplitudes of just a few frequencies over the range of temperatures.

These experiments concluded that it was possible to detect a hydrogel's phase transition by monitoring its ultrasonic properties using both reflectance and transmission measurements. The frequency shifts illustrated by the transmission measurements show both harmonic and enharmonic shifting, providing more modulation than reflectance measurements.

Example 5

Figure 8:
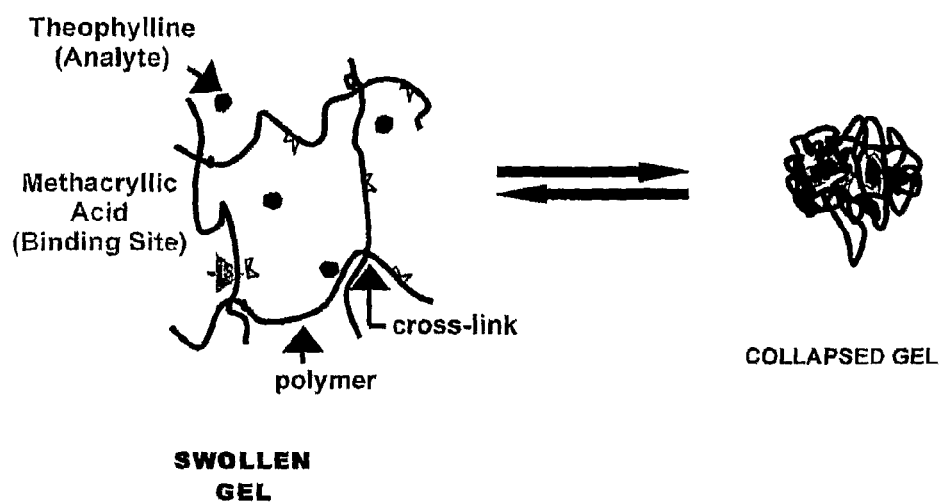
FIG. 8 is a representation of theophylline imprinted NIPA hydrogel.

The next step required the generation of a molecularly sensitive hydrogel, and test whether various concentrations of the template molecule could be detected with the clinical ultrasound system. Theophylline was chosen as the template molecule. Methacrylic acid (MAA) was deemed appropriate for the implementation of binding sites in the hydrogel, since according to work done by Seitz and Lavine, there are several sites on theophylline that attract MAA (FIG. 8).

Figure 9:
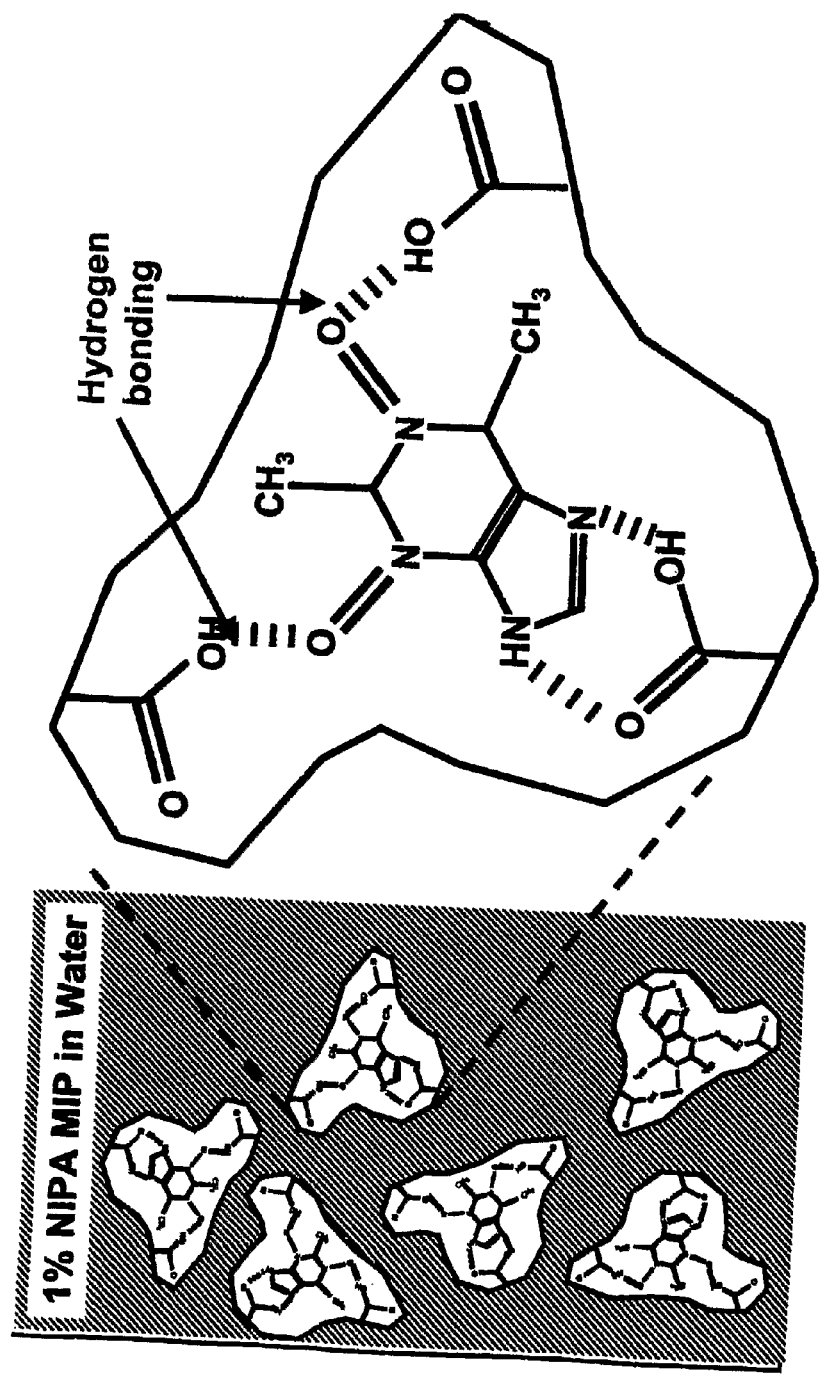
FIG. 9 is a schematic diagram of NIPA MIP polymer with theophylline.

The synthesis was achieved through a slight modification of the procedure. The procedure to molecularly imprint NIPA polymer with theophylline is the following: We added 1.0 g of NIPA monomer, 0.08 g of N,N'-methylene-bis-acrylamide (MBA), 0.08 g methacrylic acid (MAA), and 0.18 g theophylline to 99 mL of distilled water ($dH_2O$) to form a homogeneous 1 wt % NIPA solution with stirring over 3 h to ensure complete dissolution. Oxygen in the solution was purged with nitrogen gas. We then added 15 mg of ammonium persulfate to initiate the polymerization and 60 µL of tetramethylethylenediamine as an accelerator. The solution was left to polymerize for 30 minutes with gentle stirring. Once the imprinted hydrogel was formed, the theophylline template was removed by successive methylene chloride extractions. The extraction of theophylline was confirmed spectroscopically at 271 nm. All chemicals were purchased from Sigma-Aldrich (Ontario, Canada). (See schematic structure in FIG. 9). The remainder of the synthesis was carried out in the same manner as the non-imprinted NIPA.

Figure 10:
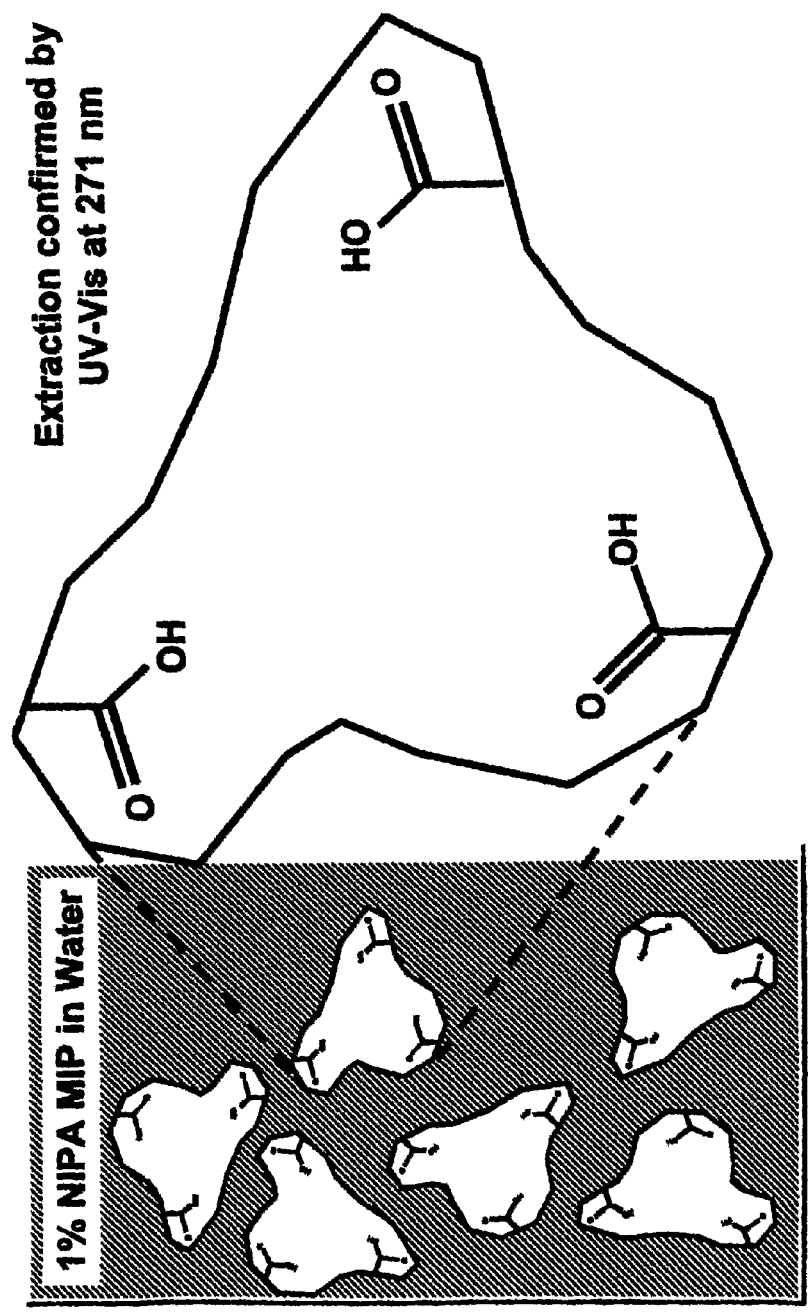
FIG. 10 is a schematic diagram of NIPA MIP polymer without theophylline

Once the hydrogel had successfully formed, removal of the theophylline template from the imprinted NIPA hydrogel was required. This was done by transferring the hydrogel solution to a separatory funnel, and adding 15-20 mL of methylene chloride ($CH_2Cl_2$) (FIG. 10). Methylene chloride is a useful solvent to use for the extraction, since it is already employed in the separation of caffeine for other applications.

Upon multiple vigorous agitations and careful venting, the entire contents of the funnel appeared opaque white. Allowing the contents to settle overnight, two distinct layers formed, a transparent upper water layer containing the imprinted NIPA hydrogel, and a lower opaque white layer containing methylene chloride and theophylline. The lower layer was drained off to isolate the imprinted NIPA hydrogel.

If the lower layer was too thick to drain efficiently, the upper layer was removed using a large volume pipette. After successful separation of imprinted NIPA and theophylline template, heat was applied to 45° C. to verify that a phase transition does indeed occur.

Example 6

Figure 11:
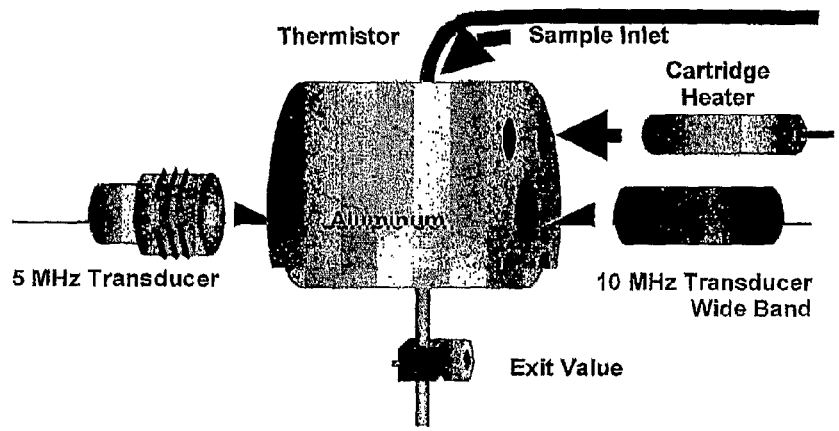
FIG. 11 is an aluminum sample cell experiment setup.

A new aluminum sample cell was designed and constructed for this experiment, and a wideband 10 MHz ultrasound probe was purchased (Optel Inc.). Mighty-Watt Cartridge heaters (Ogden Manufacturing Co.) and a temperature controller were added to the new experimental setup (FIG. 11) to more accurately control the sample cell temperature.

The external standards method was chosen to construct a theophylline calibration curve using the imprinted NIPA hydrogel, since the sample matrix, milli-q water, was easily reproducible. Each external standard had 7 mL of imprinted NIPA in water, as well as a specific amount of 0.1054 g/100 mL theophylline stock ranging from 5 µL to 200 µL. This translates to a theophylline concentration range of 4.1 to 162.5 µM.

The limitations of the SoftScope program necessitated the oscilloscope software development kit from SoftDSP, and to create software specifically for this experiment. The data acquisition program was coded in C++, and was constructed to accept acquisition parameters from MatLab. Consequently, a MatLab user interface was created to set and change acquisition parameters, as well as load and process the ultrasonic data returned by the C++ program.

Figure 12:
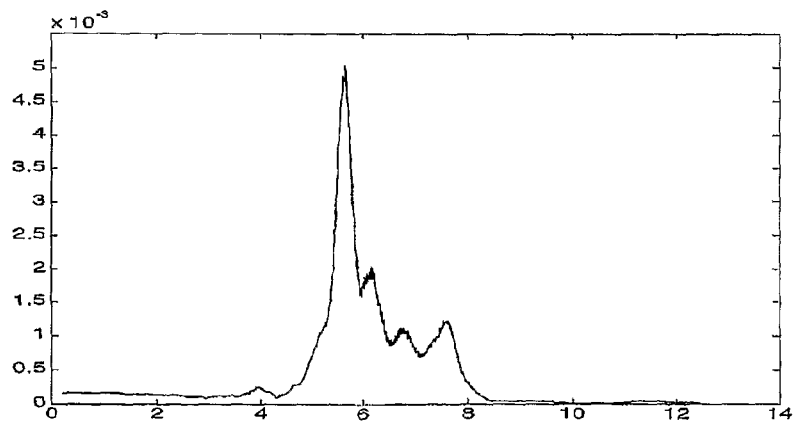
FIG. 12 is a sample FT of imprinted NIPA hyrogel with 1.7 µM theophylline at 32° C.

The standards were pulsed with the 2 MHz clinical probe, and the signal acquired using the new wideband 10 MHz probe. Instead of scanning through a range of temperatures as in the first part of the project, the samples were scanned at 32° C., 38° C., and 42° C. This was repeated three times at these three different temperatures, for a total of nine scans per standard. Finally, a sampling rate of 12.5 MHz was used, with no signal damping, and 1500 averages per scan. A sample Fourier transform of the results is given in FIG. 12.

Figure 13:
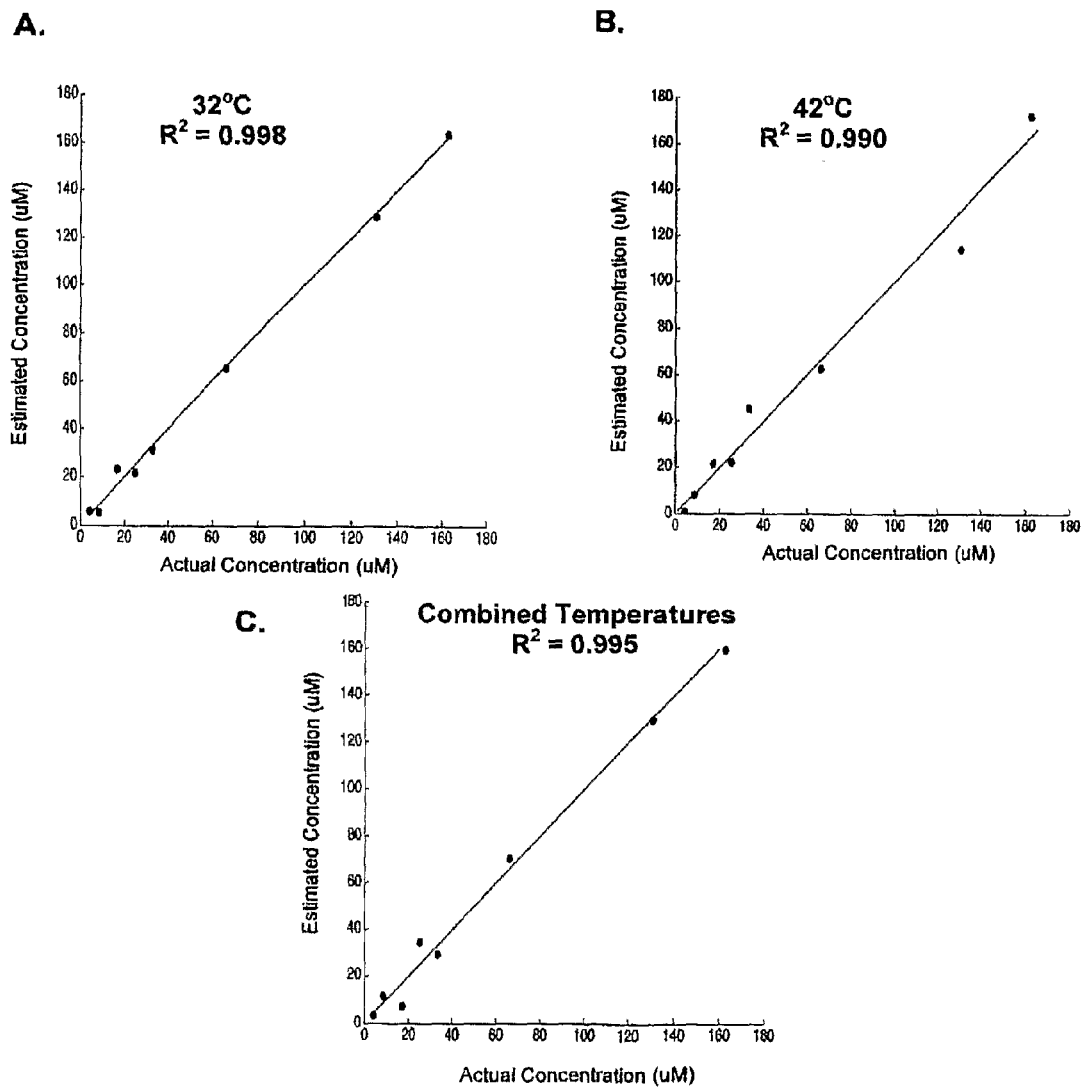
FIG. 13 is a theophylline calibration line at 32° C. (A), 42° C. (B) and combined temperatures (C)
Figure 14:
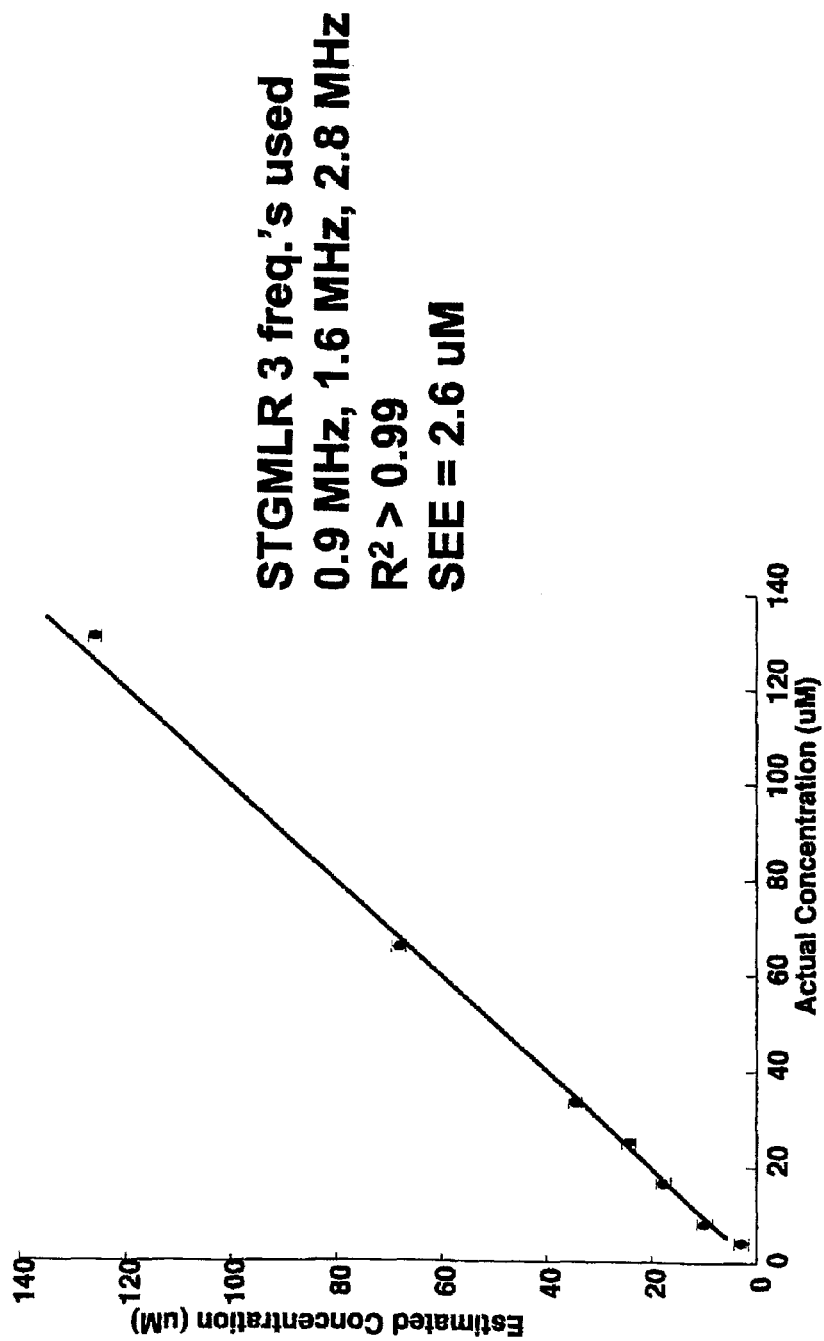
FIG. 14 is a theophylline calibration line.

These Fourier transforms were normalized with respect to the area under each curve and were fed into a stagewise multilinear regression (MLR) script for Matlab, programmed to select three wavelengths for the calibration equation. This tool iteratively calculated each regression possibility, and returned the best multilinear fit. The easiest way to visualize how well the multilinear fit coincides with the data is to view a plot of the estimated theophylline concentration from MLR, against the actual theophylline concentration of the standards. These comparisons are shown for the data acquired at 32° C., 42° C., and the combined data over the three acquisition temperatures (FIGS. 13A, B and C). The data at 38° C. is not shown as it was very similar to that taken at 42° C. It was however, included in the combined temperature analysis. A further calibration curve is shown in FIG. 14.

These results indicate that theophylline concentrations changes were detected using the imprinted NIPA hydrogel, with exceptional accuracy. It was also evident from these results that temperature was not a significant factor in determining the concentration of a theophylline solution using the imprinted NIPA hydrogel.

Figure 15:
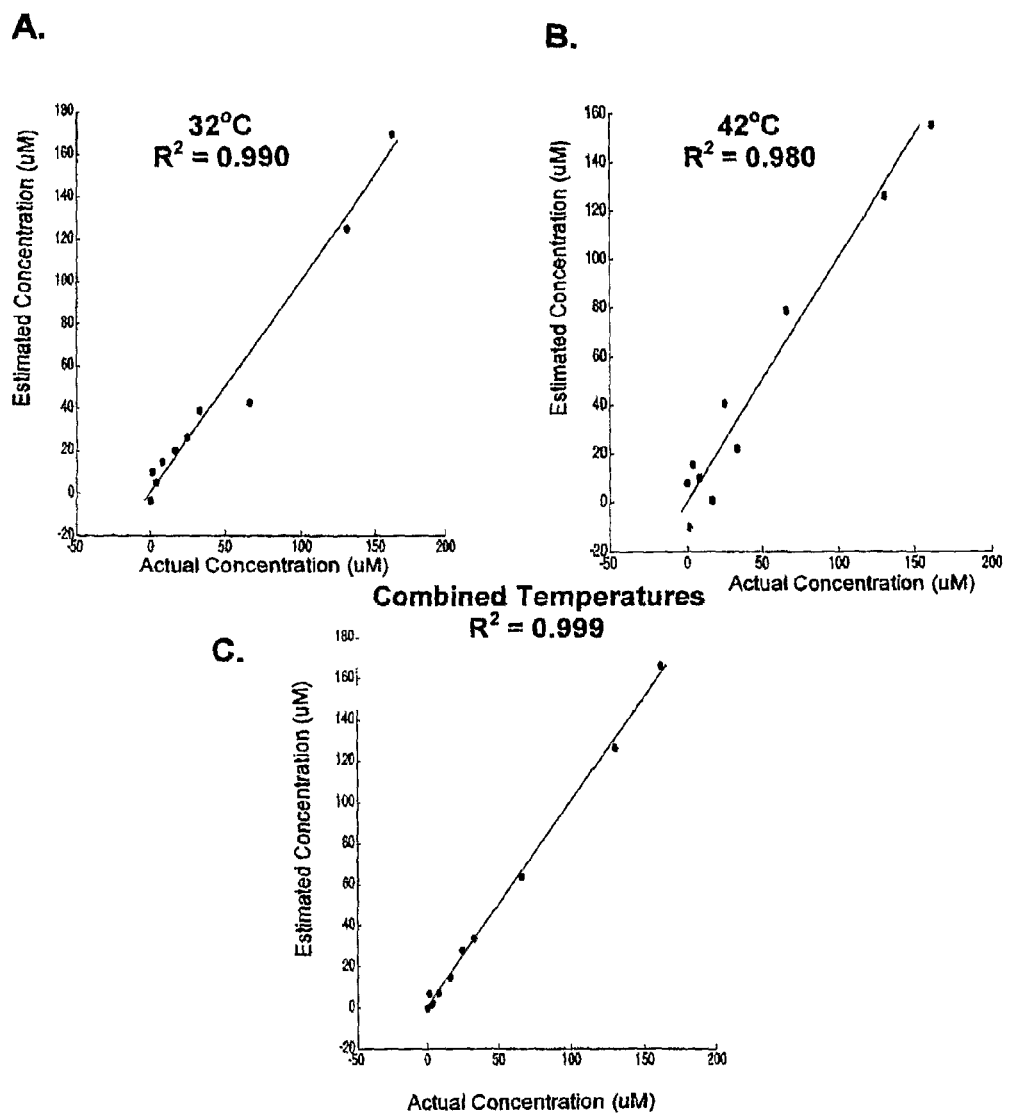
FIG. 15 is a theophylline calibration line at 32° C. (A), 42° C. (B) and combined temperatures (C)

The experiment was repeated a second time to ensure reproducibility. This time the concentration range was extended to include theophylline concentrations of 1.7 to 162.5 µM, including a blank measurement with no theophylline. This essentially covered a magnitude change of nearly 100. The data acquisition conditions were kept identical to the first experiment, and the results processed in the same manner. FIGS. 15A, B and C shows the data acquired at three previously mentioned temperatures, as well as the combined data at all temperatures.

The frequencies selected by the MLR for each temperature are shown below. The equation to calculate the concentration of theophylline based on the amplitudes at these frequencies is shown below.

TABLE 1

MLR Frequencies Chosen for Theophylline at Each Temperature

|  | 32° C. | 42° C. | Comb'd Temperatures |
|---|---|---|---|
| 1st Frequency | 5.2 MHz | 4.2 MHz | 5.2 MHz |
| 2nd Frequency | 8.2 MHz | 7.6 MHz | 8.2 MHz |
| 3rd Frequency | 7.0 MHz | 5.3 MHz | 5.5 MHz |

MLR Calibration Equations for Theophylline at Each Temperature $$\text{Conc}@32°\text{C.} = (0.26*10^5)*\text{Amp}_{Freq\,1} - (3.29*10^6) * \text{Amp}_{Freq\,2} + (0.39*10^6)*\text{Amp}_{Freq\,3} - 200$$

$$\text{Conc}@42°\text{C.} = (9.61*10^5)*\text{Amp}_{Freq\,1} + (5.99*10^5) * \text{Amp}_{Freq\,2} + (6.97*10^5)*\text{Amp}_{Freq\,3} - 0.02*10^5$$

$$\text{Conc}@\text{Comb.T.} = (0.72*10^6)*\text{Amp}_{Freq\,1} - (5.66*10^6) * \text{Amp}_{Freq\,2} - (0.07*10^6)*\text{Amp}_{Freq\,3} + 80$$

The calibration experiment again concluded that it is possible to quantify theophylline concentrations using the imprinted NIPA hydrogel. These results also seem to be largely independent of temperature, as well as being reproducible.

Example 7

Figure 16:
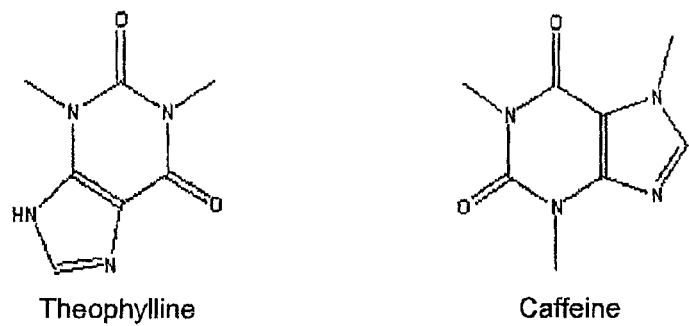
FIG. 16 is a molecular structure of theophylline and caffeine.

Caffeine and theophylline share almost identical chemical structures, with the exception of one methyl group and the placement of one π-bond (FIG. 16). This makes caffeine ideal for selectivity studies, as there are few other readily available compounds that are as similar to theophylline. The goal of this study was to see if the theophylline imprinted NIPA hydrogel was also sensitive to caffeine.

An external standards experiment was devised in the same fashion as for theophylline, except that the caffeine concentration range extended from 16.5 to 65.3 µM, including a blank measurement with no caffeine. The data was acquired using the same parameters as the for the theophylline calibration study.

Figure 17:
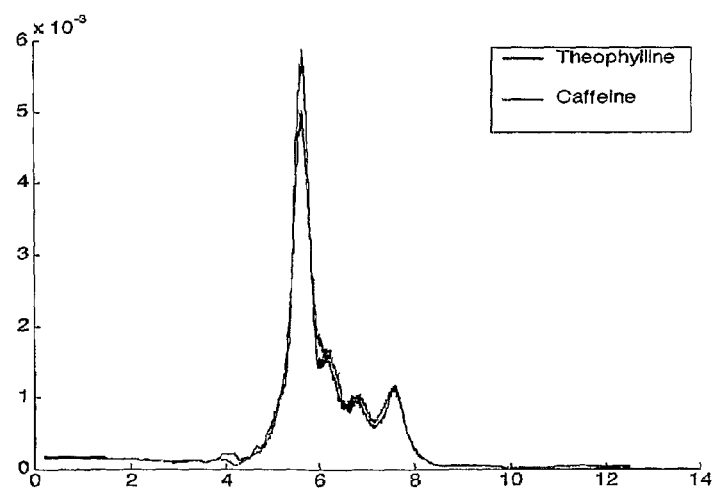
FIG. 17 are FTs of theophylline and caffeine at 16.5 µM, 32° C.

Upon first inspection of the normalized Fourier transforms, there is a subtle difference in normalized spectral profile between theophylline and caffeine of similar concentration (FIG. 17). This denotes that certain frequencies are a little more pronounced for one compound than the other.

The next step was to quantify the different frequency profiles for both compounds. This was determined by calculating the concentrations of the caffeine standards for the averaged temperature data, using the theophylline calibration equation and the amplitudes at frequencies selected for theophylline. The table listed below shows the results of these calculations.

TABLE 2

Table of Calculated and Actual Caffeine Concentrations

| Calculated Caffeine Concentrations | 174.4 µM | 161.0 µM | 93.6 µM | 253.8 µM |
|---|---|---|---|---|
| Actual Caffeine Concentrations | 0.0 µM | 16.5 µM | 32.8 µM | 65.3 µM |

It is evident that the amplitudes at the frequencies chosen for theophylline cannot be used to reliably calculate the concentration of caffeine. However, when the caffeine data was fed into the stagewise MLR program, a calibration equation was obtained. A comparison of calculated and actual caffeine concentrations showed that this equation was extremely accurate. This is due to the fact that the MLR program chose different frequencies to calculate the caffeine concentration than for theophylline. The frequencies selected when data from the three temperatures were averaged are 5.7 MHz, 6.5 MHz, and 4.2 MHz, from the most to least significant, which are quite different than those chosen for theophylline. The calibration equation is given below.

MLR Calibration Equation for Caffeine at Combined Temperatures $$\text{Conc.Avg.T.} = (1.32*10^5)*\text{Amp}_{Freq\,1} - (1.45*10^5) * \text{Amp}_{Freq\,2} + (1.06*10^3)*\text{Amp}_{Freq\,3} - 380$$

This experiment indicates that the theophylline imprinted NIPA hydrogel is not totally theophylline selective. Nevertheless, theophylline selectivity is still achieved through the careful selection of frequencies for the analysis. These frequencies have been shown to differ from those chosen for caffeine, so a simultaneous analysis of both theophylline and caffeine is theoretically highly possible.

Figure 18:
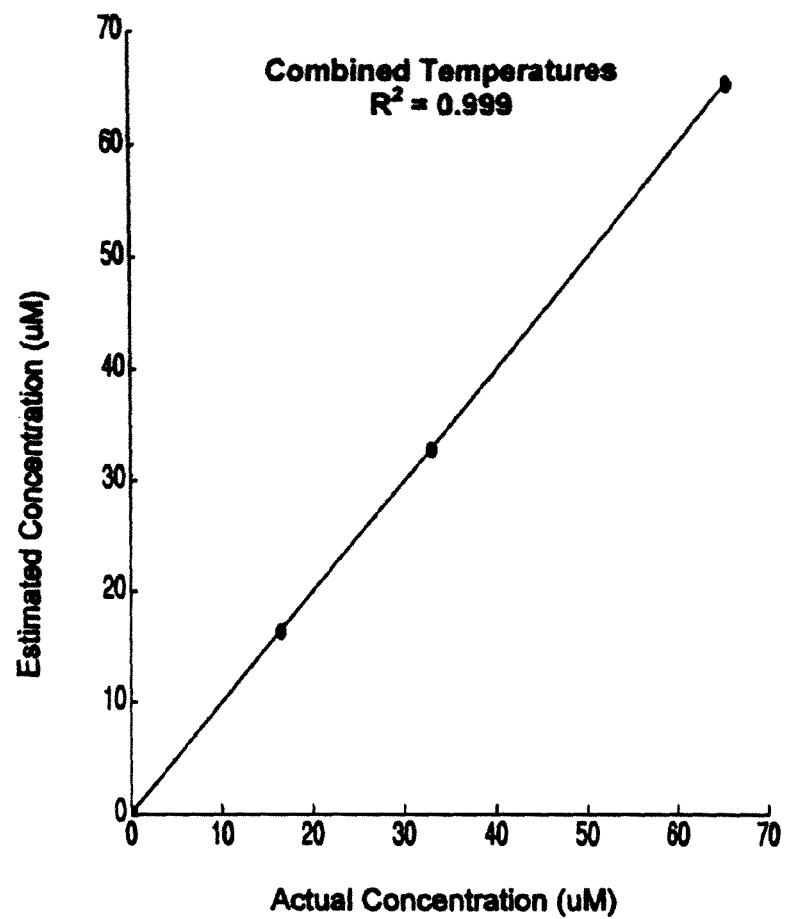
FIG. 18 is a caffeine calibration line at combined temperatures.
Figure 19:
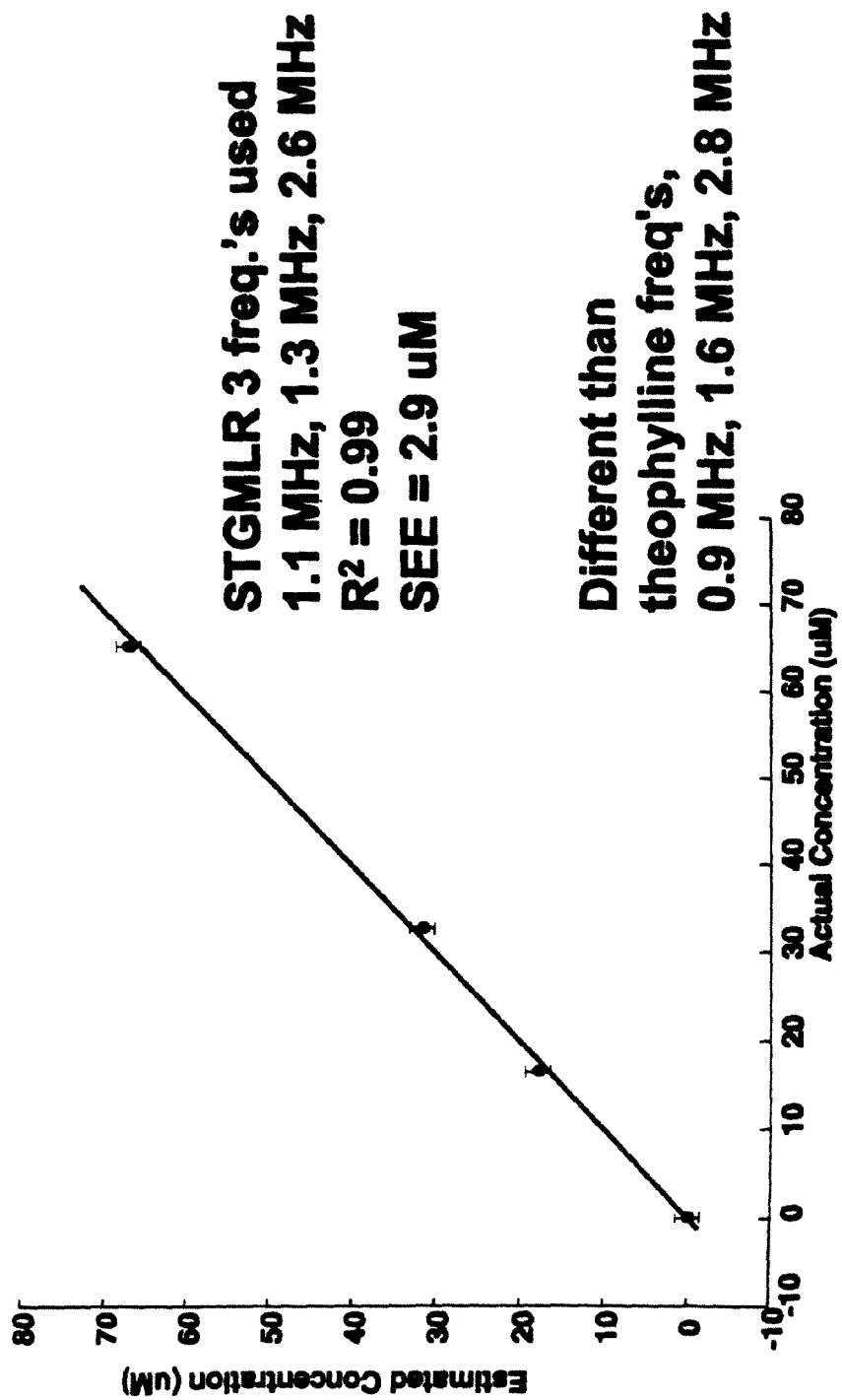
FIG. 19 is a caffeine calibration line.
Figure 20:
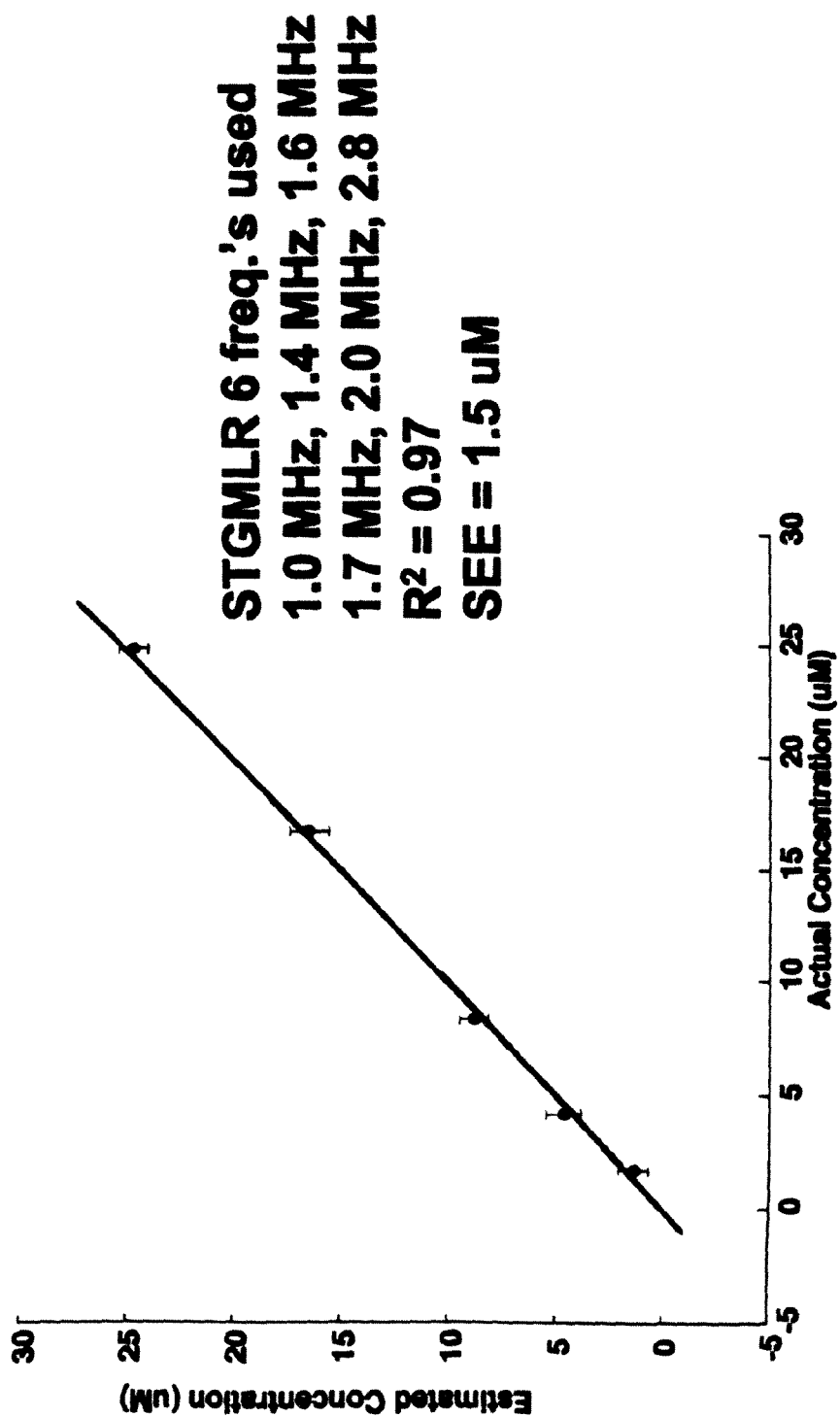
FIG. 20 is a theophylline calibration curve in the presence of caffeine.

Calibration curves for caffeine are shown in FIGS. 18 and 19 and for theophylline in the presence of caffeine in FIG. 20.

Figure 21:
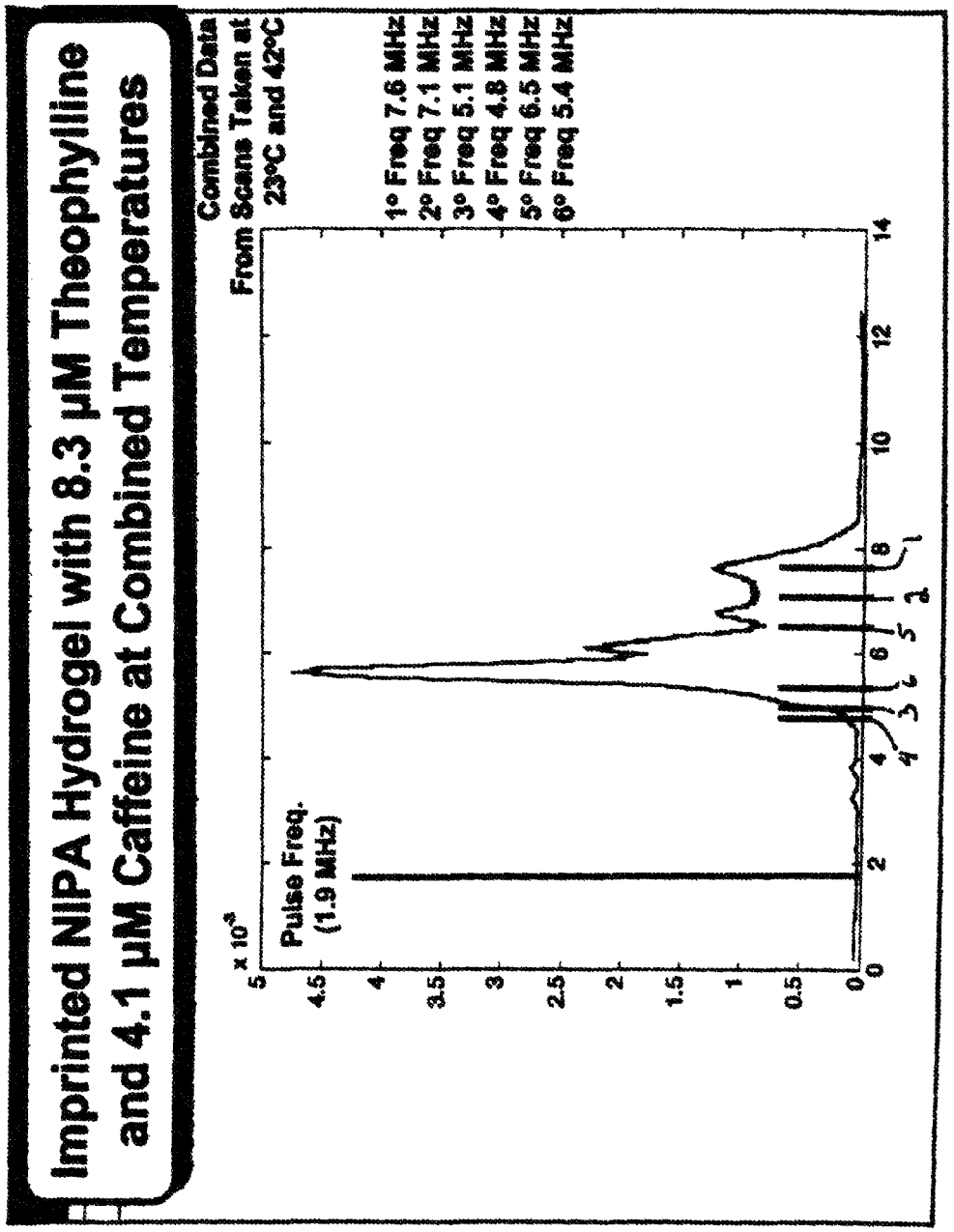
FIG. 21 is an FT of imprinted NIPA hydrogel with theophilline and caffeine.
Figure 22:
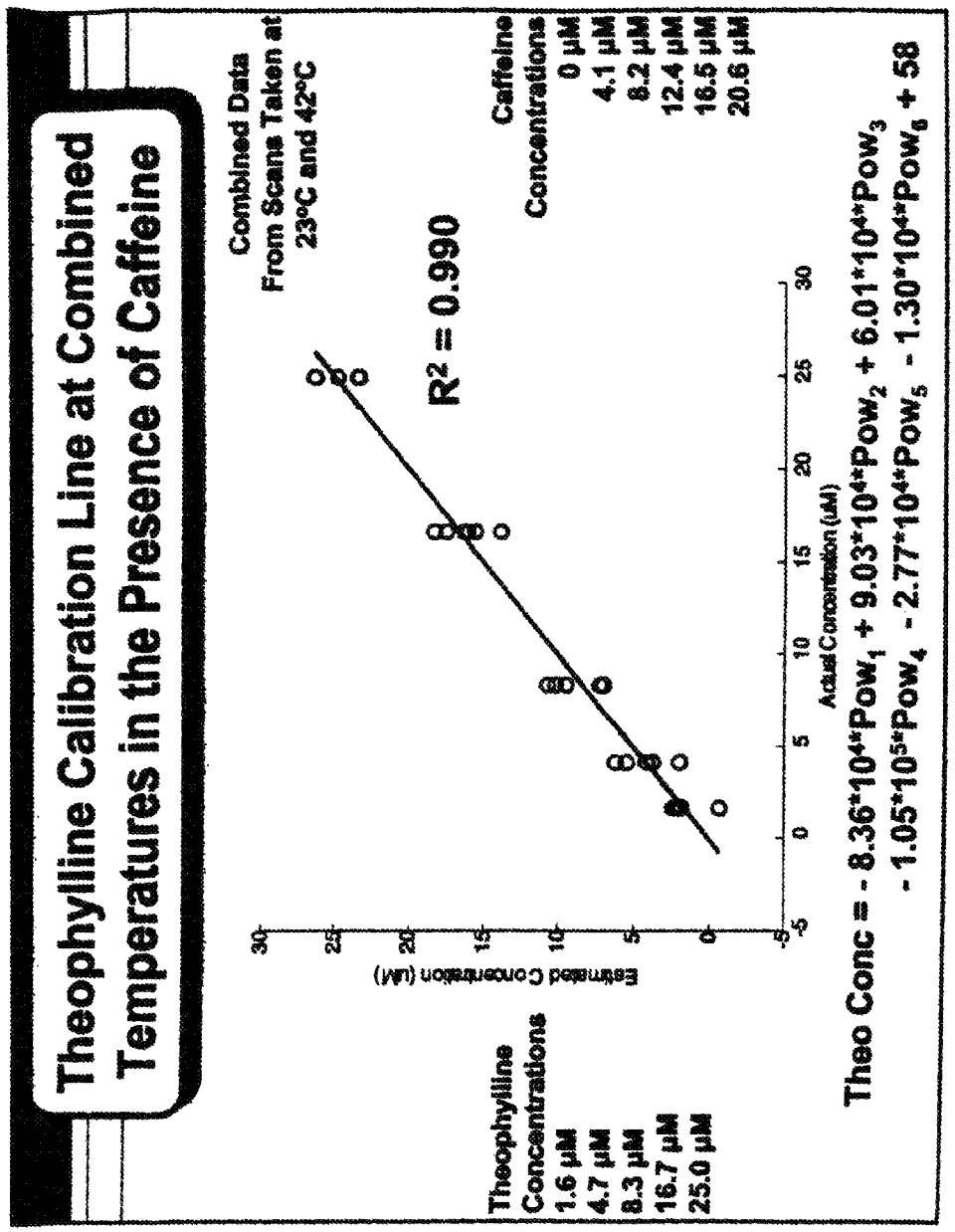
FIG. 22 is a standard curve derived for theophylline in the presence of caffeine.
Figure 23:
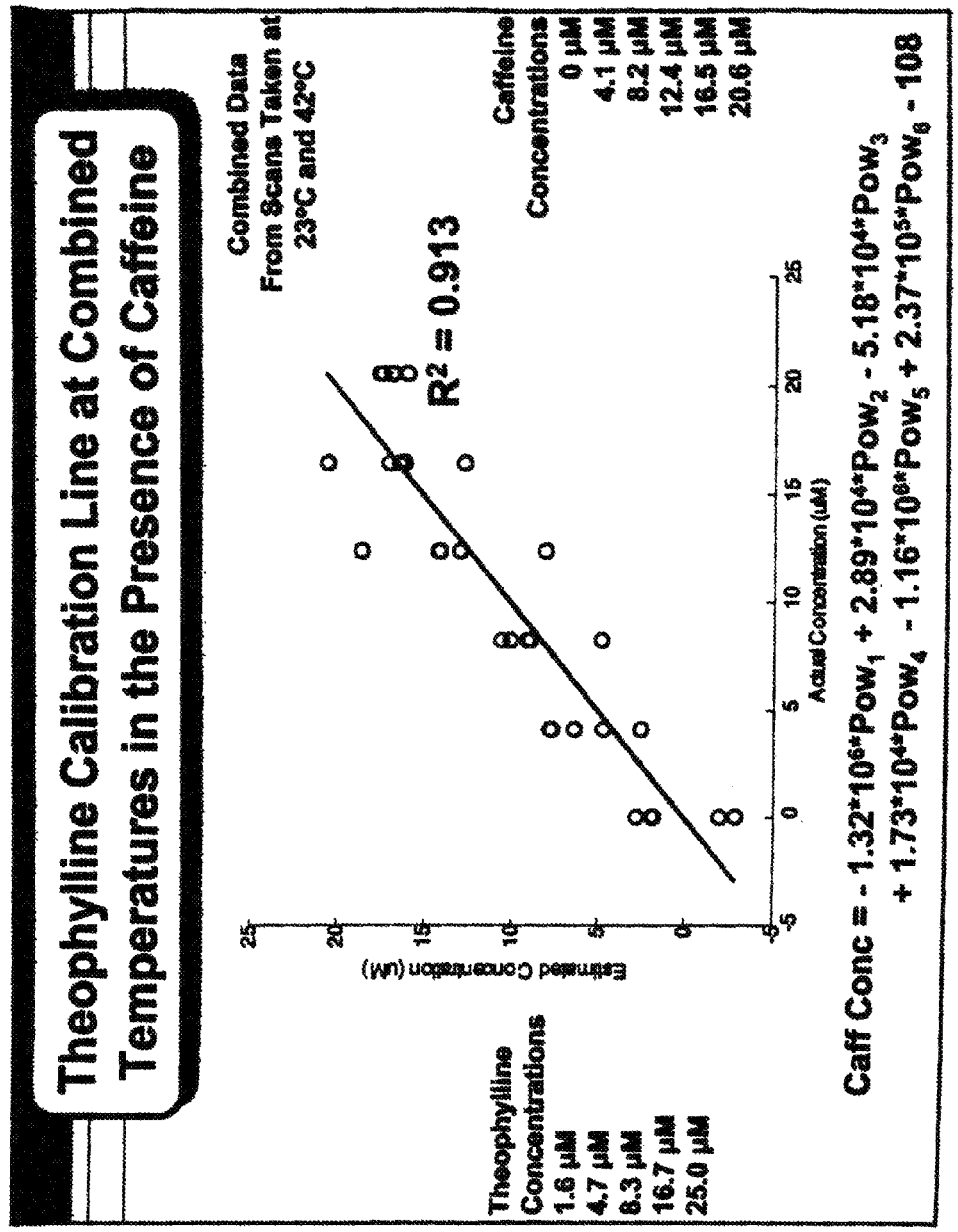
FIG. 23 is a standard curve derived for caffeine in the presence of theophylline.

It is possible to distinguish and quantify an analyte in a mixture of analytes using a single agent. This is illustrated in FIG. 21-23. In FIG. 21 a spectrum of an imprinted NIPA hydrogel in the presence of theophylline and caffeine is shown. Frequencies were derived that were used to establish a calibration curve for theophylline in the presence of caffeine (FIG. 22). The same experiment was performed to establish a caffeine calibration curve in the presence of theophilline (FIG. 23). As can be seen the results demonstrate a very good correlation between estimated and actual concentration, clearly indicating that an analyte can be quantified in the presence of other analytes.

Example 8

Figure 24:
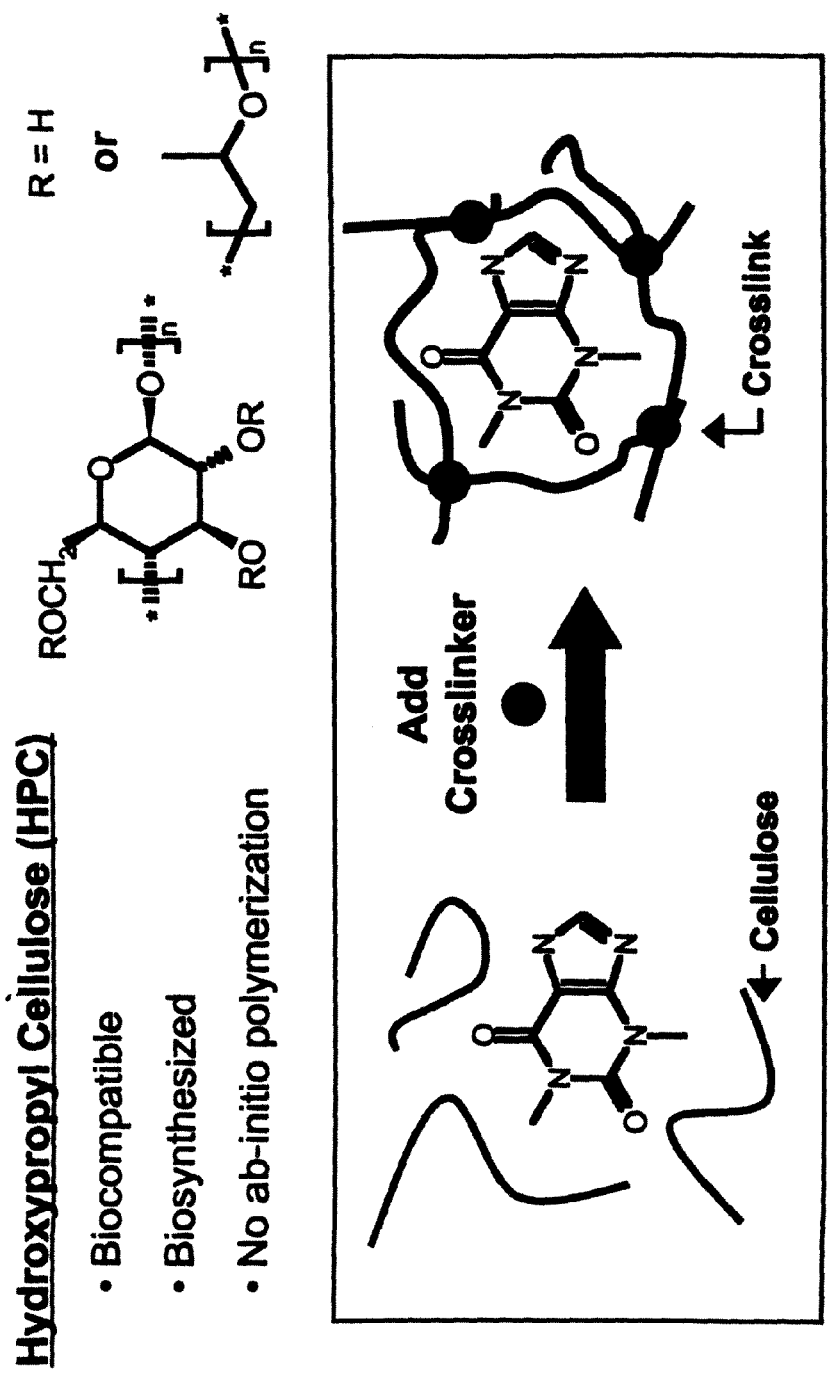
FIG. 24 is a schematic diagram of a HPC polymer.

Similar experiments were carried out using hydroxypropyl cellulose polymer (FIG. 24). The procedure to crosslink HPC is based on work by Liao et al. 1 g of HPC powder and 0.1 g of theophylline were added to 48.9 g of $dH_2O$ and stirred for 3 days, to form a homogenous 1 wt % solution of HPC with 20 mM of theophylline. 40 μL of divinylsulphone (DVS) were then added to the solution. After 3 hours of stirring, 5 drops of 1 M Sodium Hydroxide were added to the solution to raise the pH to approximately 12. The cross-linking reaction was allowed to continue for 5 hours.

The crosslinked polymers were then dialyzed against distilled water for 3 days to remove the theophylline, sodium chloride, and any free DVS.

Figure 25:
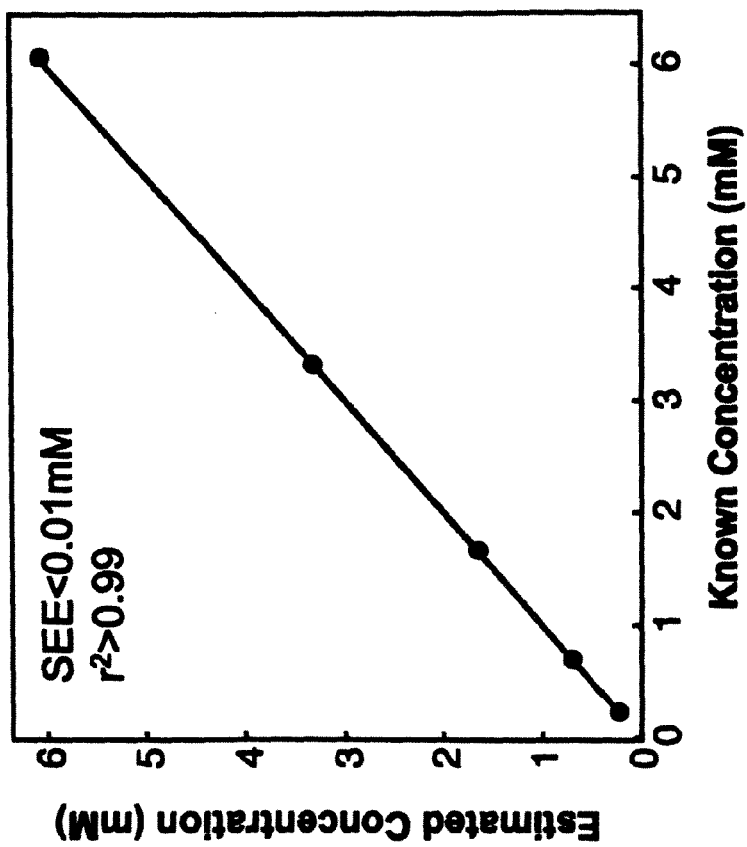
FIG. 25 is a theophylline calibration curve with HPC polymer.

FIG. 25 shows a calibration curve of theophylline. Caffeine was used as an interfering species owing to its chemical structure being nearly-identical to theophylline.

Figure 26:
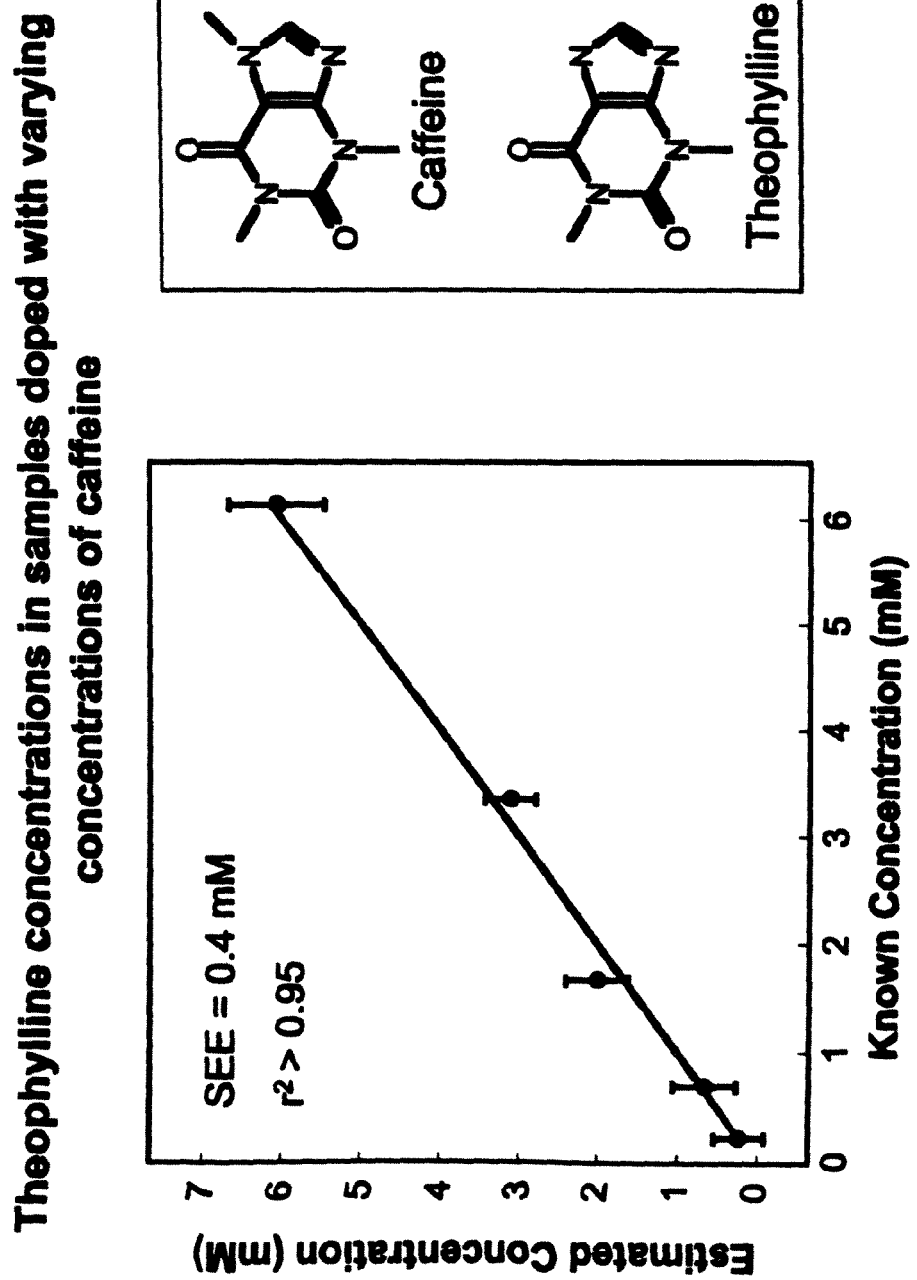
FIG. 26 is a theophylline calibration curve with caffeine.

Five sets of molecularly imprinted HPC solutions were prepared. Each set had a unique concentration of caffeine and the concentration of theophylline was varied across solutions. Likewise, the concentration of caffeine was increased from one set to another, spanning 0 to 10 mM (FIG. 26).

This data shows that it is possible to determine the concentration of theopylline using the molecular imprinting of the HPC polymer in the presence of caffeine.

Example 9

Figure 27:
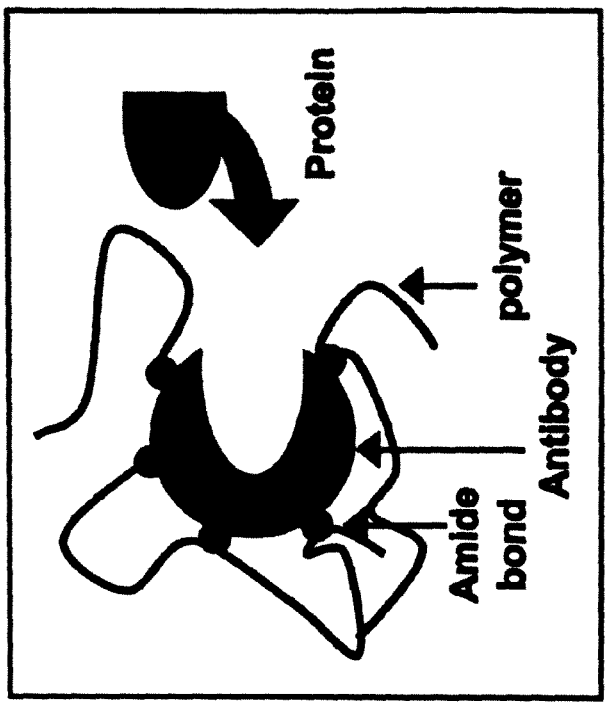
FIG. 27 is a schematic diagram of CMC polymer with antibodies.

The procedure to couple CMC and the TNFα antibody is based on work by Wheatley et al. 0.5 g of CMC powder and 0.84 g NaCl were added to 49.5 g of 0.1 M phosphate buffer, pH 6.5, and stirred for 3 days to form a homogenous 1 wt % solution of CMC. 5 mg of 1-ethyl-3-(3-dimethylaminopropyl)carbodiimide (EDC) and 3 mg of N-hydroxy-succinimide (NHS) were then added to the solution and mixed for 15 minutes. Following this, 20.6 pmol of TNFα antibodies were added to the mixture and the coupling was allowed to take place over 3 hours. The polymers were then dialyzed for 2 days to remove any unreacted coupling agent and finally the pH as adjust to 7.4 (physiological pH) (FIG. 27).

This project relies on the molecular recognition sites in the antibodies rather than recognition in the cellulose polymer. Antibodies are proteins, or long chains of amino acids, that are biosynthesized and have very specific antigen-recognition sites with binding constants typically in the $nM^{-1}$ range. These are coupled to the cellulose by the EDC mentioned above.

Figure 28:
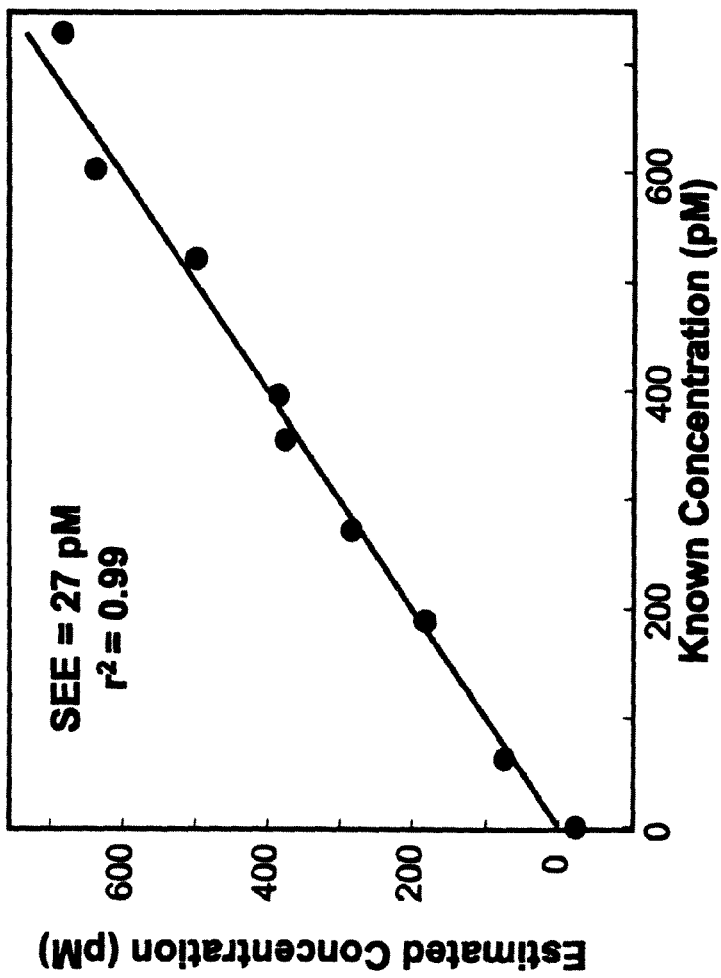
FIG. 28 is a TNF alpha calibration curve using antibodies coupled polymer.

FIG. 28 shows that it is possible to determine the concentration of the protein, TNFα, using the CMC that has been coupled to the TNFα antibodies.

Figure 29:
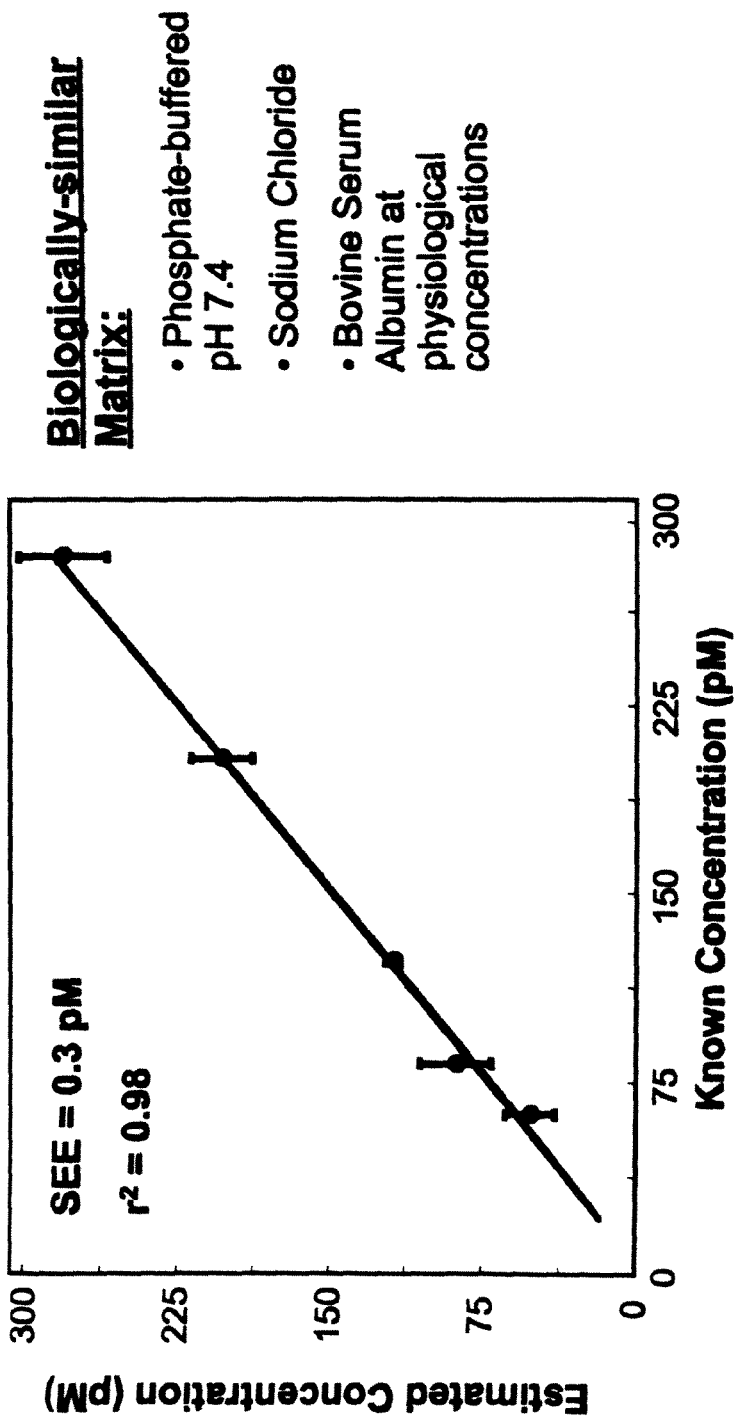
FIG. 29 is TNF alpha calibration curve in the presence of albumin.

FIG. 29 demonstrates the applicability of the antibody-coupled CMC sensor in biological/in vivo conditions. It is possible to determine the concentration of the protein, TNFα, in the presence of physiological-concentrations of serum albumin, which is the most abundant protein in blood, as well as a physiological pH.

We have used a non-cellulose dendrimer for this work (FIG. 30). There polymers form very regular spheres onto which antibodies are attached.

The procedure used to couple the antibodies to the PAMAM dendrimer is identical to that used in coupling CMC and antibodies with the exception that a 0.01 wt % gel was made (rather than a 1 wt % CMC gel, above).

Figure 31:
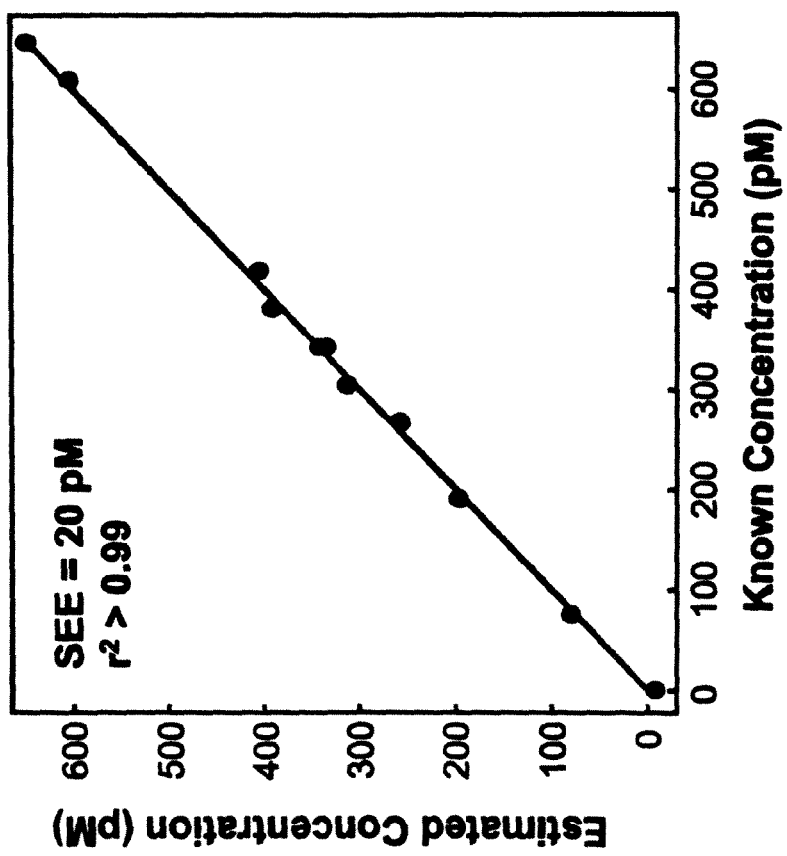
FIG. 31 is a TNF alpha calibration curve using antibodies coupled dendrimer polymer.

FIG. 31 shows that it is possible to determine the concentration of the protein, TNFα, using the PAMAM dendrimer that has been coupled to the TNFα antibodies.

Figure 32:
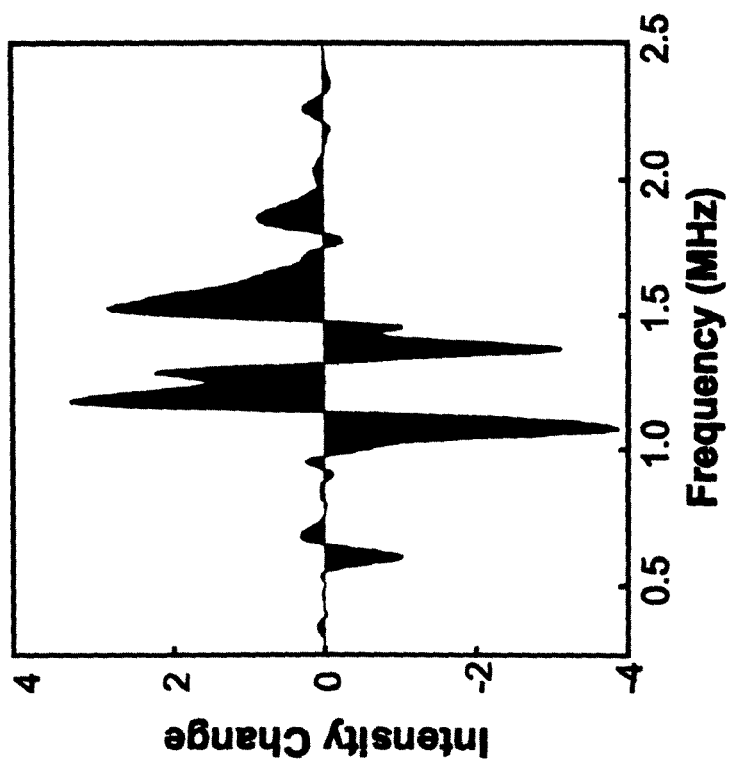
FIG. 32 is a FT of dendrimer in presence of protein.

FIG. 32 demonstrates what we believe to be a characteristic change in frequencies observed when the antibody-coupled dendrimer binds to the protein, TNFα.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A method for ultrasound contrast enhancement, comprising:
providing an ultrasound molecular sensor consisting of a hydrogel polymer with one or more target binding sites for binding one or more target molecules, said ultrasound molecular sensor having target-bound and target-unbound states wherein binding of said one or more target molecules to said ultrasound molecular sensor causes a modulation in one or more frequencies of an ultrasound signal; contacting said ultrasound molecular sensor with said one or more target molecules to produce ultrasound molecular sensor in the target-bound state; and obtaining an ultrasound signal of the target-bound ultrasound molecular sensor at one or more ultrasound frequencies wherein the signal comprises a modulation indicative of the presence of at least one target molecule.

2. The method as claimed in claim 1 wherein the modulation is selected from a relative intensity value of two or more frequencies and a shift in one or more frequencies.

3. The method as claimed in claim 1 wherein the one or more frequencies comprise anharmonic frequencies.

4. The method as claimed in claim 1, further comprising quantifying the one or more target molecule.

5. The method as claimed in claim 4 wherein the quantifying comprises: establishing a standard curve using signal amplitude of at least one frequency characteristic of the presence of the target molecule; or establishing a linear combination of signal amplitude at multiple frequencies that correlates with concentration of the target molecule.

6. The method as claimed in claim 1 wherein the target molecule binding sites are selected from an aptamer, antibody, variable regions of antibody, receptor, nucleic acids, protein or part thereof, carbohydrates, molecular imprints and combinations thereof.

7. The method as claimed in claim 1 wherein two or more target molecules are simultaneously detected.

8. The method as claimed in claim 7 wherein two or more ultrasound molecular sensors are used to detect the target molecules.

9. The method as claimed in claim 1 wherein said detection is performed in a sample obtained from a subject and said sample is a blood sample.

10. The method as claimed in claim 1 further comprising administering the ultrasound molecular sensor to a subject and wherein the detection of the target molecule is performed in situ.

11. The method as claimed in claim 10 wherein said administration is selected from either of enteral and parenteral.

12. The method as claimed in claim 1, wherein the hydrogel polymer is selected from polyacrylamide, cellulose and alginate.

13. The method as claimed in claim 1 wherein the hydrogel polymer is selected from isopropylacrilimide (NIPA), hydroxypropyl cellulose (HPC) and carboxymethyl cellulose (CMC).

* * * * *